United States Patent [19]

Schurter et al.

[11] Patent Number: 5,523,311
[45] Date of Patent: Jun. 4, 1996

[54] PROCESS AND A COMPOSITION FOR IMMUNIZING PLANTS AGAINST DISEASE

[75] Inventors: Rolf Schurter, Binningen; Walter Kunz, Oberwil; Robert Nyfeler, Basel, all of Switzerland

[73] Assignee: Ciba-Geigy Corporation, Tarrytown, N.Y.

[21] Appl. No.: 405,488

[22] Filed: Mar. 14, 1995

Related U.S. Application Data

[60] Continuation of Ser. No. 979,571, Nov. 20, 1992, abandoned, which is a division of Ser. No. 683,582, Apr. 10, 1991, Pat. No. 5,190,928, which is a continuation of Ser. No. 494,190, Mar. 15, 1990, abandoned, which is a division of Ser. No. 234,241, Aug. 18, 1988, Pat. No. 4,931,581.

[30] Foreign Application Priority Data

Aug. 21, 1987 [CH] Switzerland ............................. 3229/87

[51] Int. Cl.$^6$ .......................... C07D 285/14; A01N 43/82
[52] U.S. Cl. ............................................. 548/361; 548/126
[58] Field of Search ............................. 548/126; 514/361

[56] References Cited

FOREIGN PATENT DOCUMENTS 1176799  1/1970  United Kingdom ................... 548/126

Primary Examiner—Robert Gerstl
Attorney, Agent, or Firm—Edward McC. Roberts

[57] ABSTRACT

A method and composition for the immunization of healthy useful plants against plant diseases containing as active ingredients compounds of formula

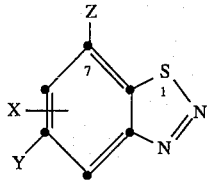

(I)

in which: X is hydrogen, halogen, hydroxy, methyl, methoxy, HOOC or MOOC; Y is hydrogen, halogen, $SO_3H$, $SO_3M$, nitro, hydroxy or amino, M being the molar equivalent of an alkali metal or alkaline earth metal ion that is formed from a corresponding base or basic compound; and Z is cyano or —CO—A; A represents either —OH or —SH, the hydrogen atom of which may also be replaced by the molar equivalent of an inorganic or organic cationic residue, or wherein A represents any other organic residue which has a molecular weight of less than 900 and which may also contain one, or more than one, hetero atom, including the salts of the phytophysiologically tolerable 7-carboxylic acid or 7-thiocarboxylic acid with primary, secondary or tertiary amines or with inorganic bases.

4 Claims, No Drawings

PROCESS AND A COMPOSITION FOR IMMUNIZING PLANTS AGAINST DISEASE

This application is a continuation of application Ser. No. 07/979,571, filed Nov. 20, 1992, now abandoned, which is a division of Ser. No. 07/683,582, filed Apr. 10, 1991, now U.S. Pat. No. 5,190,928, which is a continuation of Ser. No. 07/494,190, filed Mar. 15, 1990, now abandoned, which is a division of 07/234,241, filed Aug. 18, 1988, now U.S. Pat. No. 4,931,581.

The present invention relates to a method and composition for artificially producing in plants defence mechanisms against attack by diseases, and to measures and substances for carrying out this method.

Plants are exposed to a great variety of microbial influences by bacteria, viruses and fungi that parasiticise on the plant.

Previous efforts in the field of plant protection have as a rule been limited to strengthening the plant generally, for example by cultivation and fertilisation, and to preventing or controlling a threatened or existing disease attack by the application of safeners having a direct action (=microbicides).

The problem underlying the present invention is to activate in a gentle manner the defence mechanisms latent in a plant, so that the plant itself is able to recognise and combat an attack by a pathogen. This process may be termed immunisation.

According to the present invention the solution to the problem of controlling disease in plants lies in the artificial chemical activation of the plant's own defence mechanisms against pathogenic microbiological influences. Even a single chemical application can produce in the plant a prolonged resistance to certain pathogens lasting from several weeks to several months. The fundamental difference with respect to conventional methods of controlling disease therefore lies in the use of substances which have no microbicidal action of their own, but stimulate the plant's capacity to defend itself against microbial infections and which, as a result of their low application rates, do not harm the plant itself or the locus thereof.

The invention relates to a method for immunising plants against attack by disease, characterised by the application to the plant to be protected, to parts of the plant or to the locus thereof, of small amounts of a 7-cyano-1,2,3-benzothiadiazole derivative or a derivative of 1,2,3-benzothiadiazole-7-carboxylic acid of the formula I below.

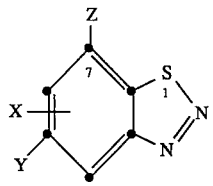
(I)

In this formula:

X is hydrogen, halogen, hydroxy, methyl, methoxy, HOOC or MOOC; Y is hydrogen, halogen, $SO_3H$, $SO_3M$, nitro, hydroxy or amino, M being the molar equivalent of an alkali metal or alkaline earth metal ion that is formed from a corresponding base or basic compound; and Z is cyano or —CO—A; wherein A represents either —OH or —SH, the hydrogen atom of which may also be replaced by the molar equivalent of an inorganic or organic cationic residue, or wherein A represents any other organic residue which has a molecular weight of less than 900 and which may also contain one, or more than one, hetero atom.

The X and Y containing 1,2,3-benzothiadizole-7-carboxylic acid of the formula I and its salts essentially constitutes the main active principle that triggers in the plant the defence mechanism against pathogens. Also included are the 7-cyano compounds covered by formula I which may undergo conversion in the plant metabolism to the 7-carboxylic acid and vice versa. It will be readily understood that the contribution to biological activity that is imparted by substituent A will be of lesser importance. Hence it may also be understood that, despite the widely differing structural variations of the substituent A, substantially equivalent biological responses will be induced with the compounds of formula I.

However, a substituent A should not hinder the active principle of the 7-substituted 1,2,3-benzothiadiazole too strongly.

Preferred substituents A are therefore cationic or any other organic residues having a molecular weight of less than 600, while those of less than 400 are especially preferred.

Among the 7-cyano compounds, those are preferred, wherein X represents hydrogen, halogen or methyl and Y represents hydrogen or halogen.

An important object of this invention is to provide the following compounds of formula I, corresponding plant protection compositions and processes for their application:

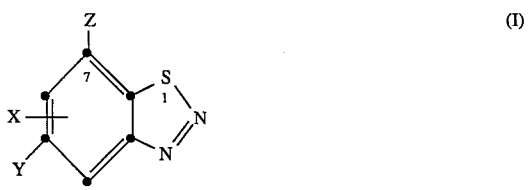
(I)

In this formula:

X is hydrogen, halogen, hydroxy, methyl, methoxy, HOOC or MOOC; Y is hydrogen, halogen, $SO_3H$, $SO_3M$, nitro, hydroxy or amino, M being the molar equivalent of an alkali metal or alkaline earth metal ion that is formed from a corresponding base or basic compound; and Z is cyano or —CO—A; A is UR, $N(R_1)R_2$ or $U^1N(=C)_n(R_3)R_4$; M is the molar equivalent of an alkali metal or alkaline earth metal ion that has been formed from a corresponding base or basic compound; U is oxygen or sulfur; $U^1$ is oxygen or —$N(R_5)$—; R is hydrogen, $C_1$–$C_8$alkyl, $C_1$–$C_8$alkyl that is substituted by halogen, cyano, nitro, hydroxy, U-$C_1$–$C_3$alkyl or by $C_2$–$C_4$dialkylamino or is interrupted by the CO group, (T)-COOH or (T)-COO$C_1$–$C_4$alkyl, $C_3$–$C_6$alkenyl, halo-substituted $C_3$–$C_6$alkenyl, $C_3$–$C_6$alkynyl, halo-substituted $C_3$–$C_6$-alkynyl, $(t)_n$-$C_3$–$C_8$cycloalkyl or a group selected from the following:

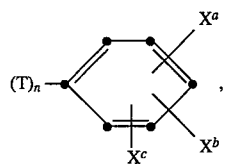

$(T)_n$-napht, $(T)_n$-Si$(C_1-C_8$-alkyl$)_3$,

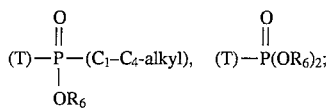

and $(T)_n$—W;

each of $X^a$, $X^b$ and $X^c$, independently of the others, is hydrogen, halogen, hydroxy, cyano, HOOC, MOOC, $C_1-C_3$alkyl-OOC, $C_1-C_4$alkyl, $C_1-C_4$alkoxy, $C_1-C_2$haloalkyl having up to 5 halogen atoms, especially fluorine atoms; or $X^a$ is $C_1-C_2$haloalkoxy having up to 5 halogen atoms, nitro, dimethylamino, phenyl, phenoxy benzyloxy sulfamoyl and $X^b$ and $X^c$ are both hydrogen; or $X^a$ is phenyl, phenoxy or benzyloxy and $X^b$ is halogen or methyl and $X^c$ is hydrogen; or $X^a$, $X^b$, and $X^c$ together are 4 or 5 fluorine atoms; naphth is a naphthyl radical that is unsubstituted or is substituted by halogen, methyl, methoxy or by nitro; W is a 5- to 7-membered saturated or unsaturated heterocycle having from 1 to 3 hetero atoms from the group O, N and S that is unsubstituted or is substituted by halogen, trifluoromethyl, cyano, $C_1-C_2$alkyl or by a $C_1-C_2$-alkoxycarbonyl-$C_1-C_4$alkyleneamino(imino) radical, or is a monosaccharide radical; T is a bridge member —$CH_2$—, —$CH_2CH_2$—, —$CH(CH_3)$—, —$CCH_3(CH_3)$—, —$CH_2CH_2CH_2$— or —$CH_2CH_2O$—; $R_1$ is hydrogen, $C_1-C_5$alkyl, $C_1-C_5$alkyl interrupted by an oxygen or sulfur atom, $C_1-C_5$alkyl substituted by halogen, cyano, HOOC or by $C_1-C_2$alkyl-OOC, $C_1-C_5$alkyl interrupted by an oxygen or sulfur atom and substituted by halogen, cyano, HOOC or by $C_1-C_2$alkyl-OOC, $C_3-C_5$alkenyl, $C_3-C_5$-alkenyl substituted by $C_1-C_3$alkyl-OOC, $C_3-C_5$alkynyl, $C_3-C_5$-alkynyl substituted by $C_1-C_3$alkyl-OOC $(T)_n$-$C_3-C_6$cycloalkyl $(T)_n$-$C_3-C_6$cycloalkyl substituted by $C_1-C_3$alkyl-OOC $(T)_n$-phenyl or $(T)_n$-phenyl substituted in the phenyl moiety by halogen, hydroxy, methyl, methoxy, $CF_3$, cyano, HOOC or by MOOC; $R_2$ is hydrogen, hydroxy, $C_1-C_3$alkyl, $C_1-C_3$alkyl substituted by cyano or by $C_1-C_3$alkoxy, $C_1-C_4$alkoxy, a 3- to 6-membered saturated or unsaturated heterocycle containing O, N or S as hetero atoms; $R_1$ and $R_2$ together are a heterocycle W; $R_3$ is hydrogen, cyano, $C_1-C_6$alkyl, phenyl, phenyl substituted by halogen, hydroxy, methyl, methoxy, HOOC or by MOOC, or a heterocycle W; $R_4$ is hydrogen, $C_1-C_6$alkyl, CONH2, CONH-CONH-$C_1-C_3$alkyl, $C_1-C_3$alkanoyl, $C_1-C_3$alkanoyl substituted by halogen or by $C_1-C_3$alkoxy, $C_3-C_5$alkenoyl, or $C_3-C_5$alkenoyl substituted by halogen or by $C_1-C_3$alkoxy; $R_3$ and $R_4$ together are a heterocycle W or a carbocyclic ring W'; W' is a carbocyclic radical having from 3 to 7 ring carbon atoms; $R_5$ is hydrogen or methyl; $R_6$ is hydrogen or $C_1-C_4$alkyl; and n is 0 or 1; and in compounds of formula I the organic radical A has a molecular weight of less than 900; and in the case where U is oxygen or sulfur, the salts of the phytophysiologically tolerable 7-carboxylic acid with primary, secondary or tertiary amines or with inorganic bases are included.

A special group of active ingredients for the method according to the invention comprises the following compounds of formula I, wherein:

X is hydrogen, halogen, hydroxy, methyl, methoxy, HOOC or MOOC; Y is hydrogen, halogen, $SO_3H$, $SO_3M$, nitro, hydroxy or amino; Z is cyano or COA; A is UR, $N(R_1)R_2$ or U1N(=C)n$(R_3)R_4$; M is the molar equivalent of an alkali metal or alkaline earth metal ion that has been formed from a corresponding base or basic compound; U is oxygen or sulfur; $U^1$ is oxygen or —N($R_5$)—; R is hydrogen, $C_1-C_8$alkyl, $C_1-C_8$alkyl substituted by halogen, cyano, nitro, hydroxy, alkoxy or by U-$C_1-C_3$alkyl, (T)-COOH or (T)-COO$C_1-C_4$alkyl, $C_2-C_6$alkenyl, halo-substituted $C_3-C_6$alkenyl, $C_3-C_6$alkynyl, halo-substituted $C_3-C_6$alkynyl, $(T)_n$-$C_3-C_8$cycloalkyl, or a group selected from the following:

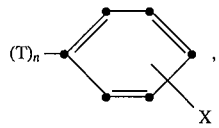

$(T)_n$-naphthyl, $(T)_n$-Si$(C_1-C_8$-alkyl$)_3$,

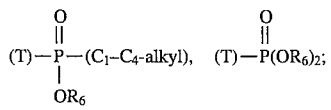

and $(T)_n$—W;

W is a 5- to 7-membered saturated or unsaturated heterocycle having from 1 to 3 hetero atoms from the group O, N and S that is unsubstituted or is substituted by halogen, trifluoromethyl, cyano, $C_1-C_2$alkyl or by a $C_1-C_2$-alkoxycarbonyl-$C_2-C_4$alkyleneimino radical, or is a monosaccharide radical; T is a bridge member —$CH_2$—, —$CH_2CH_2$—, —$CH(CH_3)$— or —$CCH_3(CH_3)$—, $R_1$ is hydrogen, $C_1-C_5$alkyl, $C_1-C_5$alkyl interrupted by an oxygen or sulfur atom, $C_1-C_5$alkyl substituted by halogen, cyano, HOOC or by $C_1-C_2$alkyl-OOC, $C_1-C_5$alkyl interrupted by an oxygen or sulfur atom and substituted by halogen, cyano, HOOC or by $C_1-C_2$alkyl-OOC, $C_3-C_5$alkenyl, $C_3-C_5$-alkenyl substituted by $C_1-C_3$alkyl-OOC, $C_3-C_5$alkynyl, $C_3-C_5$-alkynyl substituted by $C_1-C_3$alkyl-OOC, $(T)_n$-$C_3-C_6$cycloalkyl, $(T)_n$-$C_3-C_5$cycloalkyl substituted by $C_1-C_3$alkyl-OOC, $(T)_n$-phenyl or $(T)_n$-phenyl substituted in the phenyl moiety by halogen, hydroxy, methyl, methoxy, $CF_3$, cyano, HOOC or by MOOC; $R_2$ is hydrogen, hydroxy, $C_1-C_3$alkyl, $C_1-C_3$alkyl substituted by cyano or by $C_1-C_3$alkoxy, $C_1-C_4$alkoxy, or a 3- to 6-membered saturated or unsaturated heterocycle having O, N or S as hetero atoms; $R_1$ and $R_2$ together are a heterocycle W; $R_3$ is hydrogen, cyano, $C_1-C_6$alkyl, phenyl, phenyl substituted by halogen, hydroxy, methyl, methoxy, HOOC or by MOOC, or a heterocycle W; $R_4$ is hydrogen, $C_1-C_6$alkyl, $CONH_2$, CONH-CONH-$C_1-C_3$alkyl, $C_1-C_3$alkanoyl, $C_1-C_3$alkanoyl substituted by halogen or by $C_1-C_3$alkoxy, $C_3-C_5$alkenoyl, or $C_3-C_5$alkenoyl substituted by halogen or by $C_1-C_3$alkoxy; $R_3$ and $R_4$ together are a heterocycle W or a carbocyclic ring W'; W' is a carbocyclic radical having from 3 to 7 ring carbon atoms; $R_5$ is hydrogen or methyl; $R_6$ is hydrogen or $C_1-C_4$alkyl; and n is 0 or 1; and the phytophysiologically tolerable salts of the 7-carboxylic acids and 7-thiocarboxylic acids with primary, secondary and tertiary amines are included.

The present invention relates also to compositions for use against plant diseases that contain compounds of formula I as active ingredients. The invention relates also to the preparation of the said compositions and to the preparation of those active ingredients which are novel. The invention relates also to the use of the active ingredients or the compositions for protecting plants against attack by phytopathogenic microorganisms, for example fungi, bacteria and viruses.

As mentioned above, compounds of formula I are not microbicides in the conventional sense of having a direct action against the pathogens but, as can be shown hereinbelow, are in principle ineffective against such pathogens in the absence of a plant (=in vitro). When such a direct microbicidal action does nevertheless occasionally occur, it is generally an additional action brought about by certain structural elements in the molecule which superimpose such a secondary action on, but do not replace, the existing immunising effect.

The principle causing immunising action is based essentially on the specific basic 1,2,3-benzothiadiazole structure of formula I substituted in the 7-position by an acid function, whilst the ability of the 1,2,3-benzothiadiazole derivatives to penetrate the plants or their metabolism is dependent upon the radicals defined under A and the salts of the 7-acid (vehicle function).

Compounds of formula I that are therefore preferred as regards their immunising potential are those in which the organic radical A has a molecular weight of less than 600 and more especially a molecular weight of less than 400. Compounds having Z=CN are also preferred.

In a special variant, compounds of formula I preferred for plant immunisation are those in which the substituent Z is cyano or alternatively a radical A the molecular weight of which constitutes from 5.0% to 85%, preferably from 7.8% to 60%, of the molecular weight of the whole molecule of formula I.

The application rate for such immunisation agents of formula I is less than 1 kg of active ingredient/hectare, preferably less than 500 g of active ingredient/hectare, and more especially from 50 to 300 g of active ingredient/ hectare.

The term "hetero atoms" also includes elements other than N, O and S, for example Si or P.

Suitable cationic radicals for an M-OOC group are metals and organic bases. Alkali metals and alkaline earth metals are advantageous as metals, but any others may also come into consideration. Suitable organic bases are amines, especially having aliphatic, aromatic, araliphatic and/or cycloaliphatic radicals.

Halogen on its own or as a constituent of another substituent is fluorine, chlorine, bromine or iodine, preferably fluorine, chlorine or bromine. Alkyl on its own or as a constituent of another substituent is to be understood as meaning straight-chain or branched alkyl groups. Depending upon the number of carbon atoms indicated, they are, for example, the following groups: methyl, ethyl and the isomers of propyl, butyl, pentyl, hexyl, heptyl or octyl, such as, for example, isopropyl, isobutyl, tert.-butyl, sec.-butyl or isopentyl. Cycloalkyl is, for example, cyclopropyl, cyclobutyl, cyclopentyl or cyclohexyl.

Alkenyl is, for example, propen-1-yl, allyl, buten-1-yl, buten-2-yl or buten-3-yl, and chains having several double bonds. Alkynyl is, for example, propyn-2-yl, butyn-1-yl, butyn-2-yl, pentyn-4-yl, etc., preferably propargyl.

Suitable bases or compounds having basic character are inorganic bases or base formers, such as, for example, hydroxides, carbonates and hydrogen carbonates of alkali metals and alkaline earth metals, preferably LiOH, NaOH, KOH, $Mg(OH)_2$ or $Ca(OH)_2$; and also $NaHCO_3$, $KHCO_3$, $Na_2CO_3$ and $K_2CO_3$.

Heterocycles are to be understood as being, for example: furan, tetrahydrofuran, thiophene, tetrahydropyran, pyrrole, pyrrolidine, imidazole, 1,2,4-triazole, piperidine, pyridine, pyrimidine, morpholine or azacycloheptane. They are especially: furan-2-yl, tetrahydrofuran-2-yl, tetrahydrofuran-3-yl, tetrahydropyran-2-yl, 1,3-dioxolan-5-yl, pyrrol-1-yl, pyrrol-2-yl, pyrrolidin-1-yl, isoxazol-3-yl, isoxazol-4-yl, 1,2-di-thiazolin-5-yl, imidazol-1-yl, 1,2,4-triazol-1-yl, 1,3,4-triazol-1-yl, thiophen-2-yl, piperidin-1-yl, piperidin-4-yl, pyridin-2-yl, pyridin-3-yl, pyridin-4-yl, pyrimidin-2-yl, pyrimidin-4-yl, pyrimidin-5-yl, morpholin-1-yl, azacycloheptan-1-yl or benzo-1,2,3-thiadiazol-7'-yl.

Salt-forming amines are to be regarded, for example, as the following: trimethylamine, triethylamine, tripropylamine, tributylamine, tribenzylamine, tricyclohexylamine, triamylamine, trihexylamine, N,N-dimethylaniline, N,N-dimethyltoluidine, N,N-dimethyl-p-aminopyridine, N-methylpyrrolidine, N-methylpiperidine, N-methylpyrrolidine, N-methylimidazole, N-methylpyrrole, N-methylmorpholine, N-methylhexamethyleneimine, pyridine, quinoline, α-picoline, β-picoline, isoquinoline, pyrimidine, acridine, N,N,N',N'-tetramethylethylenediamine, N,N,N',N'-tetraethylethylenediamine, quinoxaline, N-propyldiisopropylamine, N,N-dimethylcyclohexylamine, 2,6-lutidine, 2,4-lutidine, triethylenediamine and heterocyclic amines of the morpholine type.

A monosaccharide radical is to be understood as being, for example, glucofuranosyl, galactopyranosyl, allofuranosyl or mannityl, the OH groups being free or acetylated or etherified by methyl, benzyl or by isopropylidenyl. Of the radicals mentioned, the diisopropylidenyl derivatives are preferred, whilst of these in turn the following radicals are especially preferred: diacetone-D-glucosidyl, 1,2,3,4-di-O-isopropylidene-D-galactopyranos-6-yl, 1,2,5,6-di-O-isopropylidene-D-mannit-3-yl, 1,2,5,6-di-O-isopropylidene-?-D-allofuranos-3-yl, D-glucofuranos-3-yl, D-galacto-pyranos-6-yl, D-mannit-3-yl, D-allofuranos-4-yl, mannopyranos-1-yl, 2-methyl-D-glucosid-6-yl, 1,2,5,6-tetraacetyl-D-galactopyranos-3-yl and 2,3,5-tribenzylribofuranos-1-yl.

As a result of their pronounced protective properties against attack by phytopathogenic microorganisms, preferred active ingredients are those of which the structures carry the following substituents or combinations of these substituents with one another:

X and Y are hydrogen; Z is cyano or COA; A is UR or $U^1N(=C)_n(R_3)R_4$; U is oxygen; $U^1$ is oxygen or $-N(R_5)-$; R is hydrogen, $C_1-C_8$alkyl, $C_1-C_8$alkyl substituted by halogen or by $C_1-C_3$-alkoxy, $C_3-C_6$alkenyl, halo-substituted $C_3-C_6$alkenyl, $C_3-C_6$alkynyl, halo-substituted $C_3-C_6$alkynyl, $(T)_n-C_3-C_8$cycloalkyl, benzyl, halogenated benzyl, methoxybenzyl, $(T)_n-Si(CH_3)_3$, $(T)-P(O)(C_1-C_4alkyl)CH_3$, $(T)-P(O)(OC_1-C_4alkyl)_2$ or the group $(T)_n-W$; W is a 5- to 7-membered saturated or unsaturated unsubstituted heterocycle having from 1 to 3 hetero atoms from the group O, N and S, or is diacetone-D-glucosidyl; T is a bridge member $-CH_2-$, $-CH_2CH_2-$, $-CH(CH_3)-$, $-CCH_3(CH_3)-$ or $-CH_2CH_2CH_2-$;

$R_3$ is hydrogen, cyano, $C_1-C_6$alkyl, phenyl or W; $R_4$ is hydrogen, $C_1-C_6$alkyl, $CONH_2$, $CONH-CONH-C_1-C_3$alkyl, $C_1-C_3$alkanoyl or $C_3-C_5$alkenoyl; $R_3$ and $R_4$ together are W or W'; W is a 5- to 7-membered saturated or unsaturated heterocycle having from 1 to 3 hetero atoms from the group O, N and S; W' is a radical from the group:

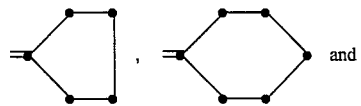 and

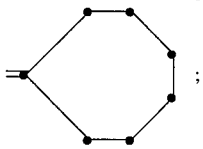

n is 0 or 1.

A special group of active ingredients having preferred microbicidal action against phytopathogenic microorganisms comprises compounds having the following substituents or combinations of these substituents with one another:

X and Y are hydrogen; Z is cyano or COA; A is UR or $U^1N(=C)_n(R_3)R_4$; U is oxygen; $U^1$ is oxygen or $-N(R_5)-$; R is hydrogen, $C_1-C_8$alkyl, $C_1-C_8$alkyl substituted by halogen or by $C_1-C_3$-alkoxy, $C_3-C_6$alkenyl, halo-substituted $C_3-C_6$alkenyl, $C_3-C_6$alkynyl, halo-substituted $C_3-C_6$alkynyl, $(T)_n$-$C_3-C_8$cycloalkyl, benzyl, halogenated benzyl, $(T)_n$-$Si(CH_3)_3$, $(T)$-$P(O)(C_1-C_4alkyl)CH_3$, $(T)$-$P(O)(OC_1-C_4alkyl)_2$ or the group $(T)_n$-W; W is a 5- to 7-membered saturated or unsaturated unsubstituted heterocycle having from 1 to 3 hetero atoms from the group O, N and S, or is diacetone-D-glucosidyl; T is a bridge member $-CH_2-$, $-CH_2CH_2-$, $-CH(CH_3)-$ or $-CCH_3(CH_3)-$; $R_3$ is hydrogen, cyano, $C_1-C_6$alkyl, phenyl or W; $R_4$ is hydrogen, $C_1-C_6$alkyl, $CONH_2$, $CONH-CONH-C_1-C_3$alkyl, $C_1-C_3$alkanoyl or $C_3-C_5$alkenoyl; $R_3$ and $R_4$ together are W or W'; W is a 5- to 7-membered saturated or unsaturated heterocycle having from 1 to 3 hetero atoms from the group O, N and S; W' is a radical from the group:

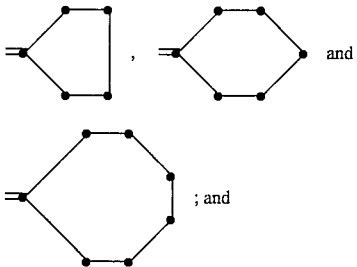

n is 0 or 1.

Most of the compounds falling within the scope of formula I are novel; the others are known. For example, German Offenlegungsschrift No. 1 695 786 and French Patent Specification No. 1 541 415 disclose some compounds in general form as biocidal active ingredients for use in herbicidal, insecticidal and fungicidal compositions. However, none of these known individual compounds falling within the scope of formula I of the present invention is specifically described as having fungicidal activity. Furthermore, benzo-1,2,3-thiadiazole-7-carboxylic acid is known from J. Chem. Soc. (C) 1971, 3997, but no details of biological properties are given.

The novel compounds of the present invention are defined in the following groups:

Compounds of formula I'

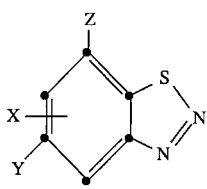

in which:

X is hydrogen, halogen, hydroxy, methyl, methoxy, HOOC or MOOC; Y is hydrogen, halogen, $SO_3H$, $SO_3M$, nitro, hydroxy or amino; Z is cyano or COA; A is UR, $N(R_1)R_2$ or $U^1N(=C)_n(R_3)R_4$; M is the molar equivalent of an alkali metal or alkaline earth metal ion that has been formed from a corresponding base or basic compound; U is oxygen or sulfur; $U^1$ is oxygen or $-N(R_5)-$; R is hydrogen, $C_1-C_8$alkyl, $C_1-C_8$alkyl substituted by halogen, cyano, nitro, hydroxy or by $U-C_1-C_3$alkyl, $(T)$-COOH or $(T)$-COOC$_1$-C$_4$alkyl, $C_3-C_6$alkenyl, halo-substituted $C_3-C_6$alkenyl, $C_3-C_6$alkynyl, halo-substituted $C_3-C_6$alkynyl, $(T)_n$-$C_3-C_8$cycloalkyl, or a group selected from the following:

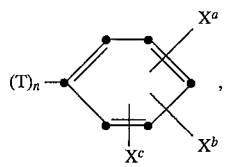

$(T)_n$-napht, $(T)_n$-Si$(C_1-C_8$-alkyl$)_3$,

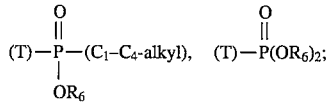

and $(T)_n$—W;

each of $X^a$ $X^b$ and $X^c$ independently of the others is hydrogen, halogen hydroxy, cyano, HOOC, MOOC, $C_1-C_3$alkyl-OOC, $C_1-C_4$alkyl, $C_1-C_4$alkoxy, $C_1-C_2$haloalkyl having up to 5 halogen atoms, especially fluorine atoms; or $X^a$ is $C_1-C_2$haloalkoxy having up to 5 halogen atoms, nitro, dimethylamino, phenyl, phenoxy benzyloxy or sulfamoyloxy and $X^b$ and $X^c$ are both hydrogen; or $X^a$ is phenyl, phenoxy or benzyloxy and $X^b$ is halogen or methyl and $X^c$ is hydrogen; or $X^a$, $X^b$ and $X^c$ together are 4 or 5 fluorine atoms; naphth is a naphthyl radical that is unsubstituted or is substituted by halogen, methyl, methoxy or by nitro; W is a 5- to 7-membered saturated or unsaturated heterocycle having from 1 to 3 hetero atoms from the group O, N and S that is unsubstituted or is substituted by halogen, trifluoromethyl, cyano, $C_1-C_2$alkyl or by a $C_1-C_2$-alkoxycarbonyl-C 2-$C_4$alkyleneimino radical, or is a monosaccharide radical; T is a bridge member $-CH_2-$, $-CH_2CH_2-$, $-CH(CH_3)-$, $-CH_2CH_2CH_2-$ or $-CH_2CH_2O-$; $R_1$ is hydrogen, $C_1-C_5$alkyl, $C_1-C_5$alkyl interrupted by an oxygen or sulfur atom, $C_1-C_5$alkyl substituted by halogen, cyano, HOOC or by $C_1-C_2$alkyl-OOC, $C_1-C_5$alkyl interrupted by an oxygen or sulfur atom and substituted by halogen, cyano. HOOC or by $C_1-C_2$alkyl-OOC, $C_3-C_5$alkenyl, $C_3-C_5$-alkenyl substituted by $C_1-C_3$alkyl-OOC, $C_3-C_5$alkynyl, $C_3-C_5$-alkynyl substituted by $C_1-C_3$alkyl-OOC, $(T)_n$-$C_3-C_6$cycloalkyl, $(T)_n$-$C_3-C_6$cycloalkyl substituted by $C_1-C_3$alkyl-OOC, $(T)_n$-phenyl or $(T)_n$-phenyl substituted in the phenyl moiety by halogen, hydroxy, methyl, $CF_3$, cyano, methoxy, HOOC or by MOOC; $R_2$ is hydrogen, hydroxy, $C_1$–$C_3$alkyl, $C_1$–$C_3$alkyl substituted by cyano or by $C_1$–$C_3$alkoxy, $C_1$–$C_4$alkoxy, or a 3- to 6-membered saturated or unsaturated heterocycle having O, N or S as hetero atoms; $R_1$ and $R_2$ together are a heterocycle W; $R_3$ is hydrogen, cyano, $C_1$–$C_6$alkyl, phenyl, phenyl substituted by halogen, hydroxy, methyl, methoxy, HOOC or by MOOC, or a heterocycle W; $R_4$ is hydrogen, $C_1$–$C_6$alkyl, $CONH_2$, CONH-CONH-$C_1$–$C_3$alkyl, $C_1$–$C_6$alkanoyl, $C_1$–$C_3$alkanoyl substituted by halogen or by $C_1$–$C_3$alkoxy, $C_3$–$C_5$alkenoyl, or $C_3$–$C_5$alkenoyl substituted by halogen or by $C_1$–$C_3$alkoxy; $R_3$ and $R_4$ together are a heterocycle W or a carbocyclic ring W'; W' is a carbocyclic radical having from 3 to 7 ring carbon atoms; $R_5$ is hydrogen or methyl; $R_6$ is hydrogen or $C_1$–$C_4$alkyl; and n is 0 or 1;

1) with the exception of the compounds:
7-cyanobenzo-1,2,3-thiadiazole; 4-chloro-7-cyanobenzo-1,2,3-thiadiazole; 4,6-dibromo-7-cyanobenzo-1,2,3-thiadiazole; benzo-1,2,3-thiadiazole-7-carboxylic acid; benzo-1,2,3-thiadiazole-7-carboxylic acid methyl ester; or 2) with the proviso that if Z is cyano, HOOC or methoxycarbonyl, each of X and Y, independently of the other, is not hydrogen, chlorine or bromine; or 3) with the proviso that if Z is cyano, methoxycarbonyl, ethoxycarbonyl or HOOC, X is not hydrogen, halogen, hydroxy, methyl or methoxy and Y is not hydrogen, halogen, nitro or amino; or 4) with the proviso that if Z is cyano, $C_1$–$C_4$alkoxycarbonyl or HOOC, X is not hydrogen, halogen, hydroxy, methyl or methoxy and Y is not hydrogen, halogen, nitro or amino.

A special group of novel active ingredients comprises the following compounds of formula I' in which:

X is hydrogen, halogen, hydroxy, methyl, methoxy, HOOC or MOOC; Y is hydrogen, halogen, $SO_3H$, $SO_3M$, nitro, hydroxy or amino; Z is cyano or COA; A is UR, $N(R_1)R_2$ or $U^1N(=C)_n(R_3)R_4$; M is the molar equivalent of an alkali metal or alkaline earth metal ion that has been formed from a corresponding base or basic compound; U is oxygen or sulfur; $U^1$ is oxygen or —N($R_5$)—; R is hydrogen, $C_1$–$C_8$alkyl, $C_1$–$C_8$alkyl that is substituted by halogen, cyano, nitro, hydroxy, alkoxy or by U-$C_1$–$C_3$alkyl, (T)-COOH or (T)-COO$C_1$–$C_4$alkyl, $C_2$–$C_6$alkenyl, halo-substituted $C_3$–$C_4$alkenyl, $C_3$–$C_6$alkynyl, halo-substituted $C_3$–$C_6$alkynyl, $(T)_n$-$C_3$–$C_8$cycloalkyl, or a group selected from the following:

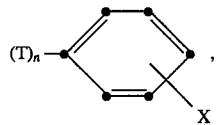

$(T)_n$-naphthyl, $(T)_n$-Si($C_1$–$C_8$-alkyl)$_3$,

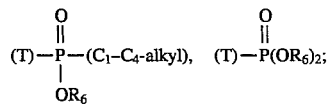

and $(t)_n$—W; W is a 5- to 7-membered saturated or unsaturated heterocycle having from 1 to 3 hetero atoms from the group O, N and S that is unsubstituted or is substituted by halogen, trifluoromethyl, cyano, $C_1$–$C_2$alkyl or by a $C_1$–$C_2$-alkoxycarbonyl-$C_2$–$C_4$alkyleneimino radical, or is a monosaccharide radical; T is a bridge member —$CH_2$—, —$CH_2CH_2$— or —CH($CH_3$)—; $R_1$ is hydrogen, $C_1$–$C_5$alkyl, $C_1$–$C_5$alkyl interrupted by an oxygen or sulfur atom, $C_1$–$C_5$alkyl substituted by halogen, cyano, HOOC or by $C_1$–$C_2$alkyl-OOC, $C_1$–$C_5$alkyl interrupted by an oxygen or sulfur atom and substituted by halogen, cyano, HOOC or by $C_1$–$C_2$alkyl-OOC, $C_3$–$C_5$alkenyl, $C_3$–$C_5$-alkenyl substituted by $C_1$–$C_3$alkyl-OOC, $C_3$–$C_5$alkynyl, $C_3$–$C_5$-alkynyl substituted by $C_1$–$C_3$alkyl-OOC, $(T)_n$-$C_3$–$C_6$cycloalkyl, $(T)_n$-$C_3$–$C_6$cycloalkyl substituted by $C_1$–$C_3$alkyl-OOC, $(T)_n$-phenyl or $(T)_n$-phenyl substituted in the phenyl moiety by halogen, hydroxy, methyl, $CF_3$, cyano, methoxy, HOOC or by MOOC; $R_2$ is hydrogen, hydroxy, $C_1$–$C_3$alkyl, $C_1$–$C_3$alkyl substituted by cyano or by $C_1$–$C_3$alkoxy, $C_1$–$C_4$alkoxy, or a 3- to 6-membered saturated or unsaturated heterocycle containing O, N or S as hetero atoms; $R_1$ and $R_2$ together are a heterocycle W; $R_3$ is hydrogen, cyano, $C_1$–$C_6$alkyl, phenyl, phenyl substituted by halogen, hydroxy, methyl, methoxy, HOOC or by MOOC, or a heterocycle W; $R_4$ is hydrogen, $C_1$–$C_6$alkyl, $CONH_2$, CONH-CONH-$C_1$–$C_3$alkyl, $C_1$–$C_3$alkanoyl, $C_1$–$C_3$alkanoyl substituted by halogen or by $C_1$–$C_3$alkoxy, $C_3$–$C_5$alkenoyl, or $C_3$–$C_5$alkenoyl substituted by halogen or by $C_1$–$C_3$alkoxy; $R_3$ and $R_4$ together are a heterocycle W or a carbocyclic ring W'; W' is a carbocyclic radical having from 3 to 7 ring carbon atoms; $R_5$ is hydrogen or methyl; $R_6$ is hydrogen or $C_1$–$C_4$alkyl; and n is 0 or 1;

with the exception of the compounds:
7-cyanobenzo-1,2,3-thiadiazole; 4-chloro-7-cyanobenzo-1,2,3-thiadiazole; 4,6-dibromo-7-cyanobenzo-1,2,3-thiadiazole: benzo-1,2,3-thiadiazole-7-carboxylic acid; benzo-1,2,3-thiadiazole-7-carboxylic acid methyl ester.

The following compounds are preferred as active ingredients because of their excellent biological activity:

Group A (known compounds)
7-carboxylic acid-benzo-1,2,3-thiadiazole (Compound 1.1); 7-methoxycarbonylbenzo-1,2,3-thiadiazole (Compound 1.2).

Group B 1 (novel compounds)
7-ethoxycarbonylbenzo-1,2,3-thiadiazole (Compound 1.3); 7-n-propoxycarbonylbenzo-1,2,3-thiadiazole (Compound 1.4); 7-isopropoxycarbonylbenzo-1,2,3-thiadiazole (Compound 1.5); 7-n-butoxycarbonylbenzo-1,2,3-thiadiazole (Compound 1.6); 7-sec.-butoxycarbonylbenzo-1,2,3-thiadiazole (Compound 1.7); 7-tert.-butoxycarbonylbenzo-1,2,3-thiadiazole (Compound 1.8); 7-cyclopropylmethoxycarbonylbenzo-1,2,3-thiadiazole (Compound 1.28); 7-(2'-phenethoxycarbonyl)-benzo-1,2,3-thiadiazole (Compound 1.33); 7-benzyloxycarbonylbenzo-1,2,3-thiadiazole (Compound 1.34); 7-allyloxycarbonyl-benzo-1,2,3-thiadiazole (Compound 1.44); 7-propyn-2-yloxycarbonylbenzo-1,2,3-thiadiazole (Compound 1.46); N-ethylaminocarbonyl-2-cyano-2-oximinocarbonylbenzo-1,2,3-thiadiazol-7-ylacetamide (Compound 1.78); sodium salt of benzo-1,2,3-thiadiazole-7-carboxylic acid (Compound 1.112); potassium salt of benzo-1,2,3-thiadiazole-7-carboxylic acid (Compound 1.113); triethylammonium salt of benzo-1,2,3-thiadiazole-7-carboxylic acid (Compound 1.114); 7-(1-phenethoxycarbonyl)-benzo-1,2,3-thiadiazole (Compound 1.119); 7-(1-naphthylmethoxycarbonyl)-benzo-1,2,3-thiadiazole (Compound 1.116); 7-(methylthiocarbonyl)-benzo-1,2,3-thiadiazole (Compound 2.1); 7-(ethylthiocarbonyl)-benzo-1,2,3-thiadiazole (Compound 2.2); 7-(benzylthiocarbonyl)-benzo-1,2,3-thiadiazole (Compound 2.5); 7-[(dicyanomethyl)-aminocarbonyl]-benzo-1,2,3-thiadiazole (Compound 3.13); 1-amino-N-[(1,3,4-thiadiazol-2-yl)-(N-benzo-1,2,3-thiadiazoyl)]-2-methoxycarbonyl-1-propene (Compound 3.28); 1-amino-N-! (1,3,4-thiadiazol-2-yl)-(N-benzo-1,2,3-thiadiazoyl)]-2-methoxycarbonyl-1-butene (Compound 3.29); 1-(benzo-1,2,3-thiadiazole-7-carbonyl)-2-(α-methylpropylidene)-hydrazine (Compound 4.2); 1-(benzo-1,2,3-thiadiazole-7-carbonyl)-2-(cyclobutylidene)-hydrazine (Compound 4.8); 1-(benzo-1,2,3-thiadiazole-7-carbonyl)-2-(cyclopentylidene)-hydrazine (Compound 4.9); 1-(benzo-1,2,3-thiadiazole-7-carbonyl)-2-(cyclohexylidene)-hydrazine (Compound 4.10); 2-(benzo-1,2,3-thiadiazole-7-carbonyl)-1-(2'-sec.-butyl)-hydrazine (Compound 5.2); 1-(benzo-1,2,3-thiadiazole-7-carbonyl)-2-(cyclopentyl)-hydrazine (Compound 5.7); 1-(benzo-1,2,3-thiadiazole-7-carbonyl)-2-(cyclohexyl)-hydrazine (Compound 5.8); 1-(benzo-1,2,3-thiadiazole-7-carbonyl)-2-(cycloheptyl)-hydrazine (Compound 5.9); 1-(benzo-1,2,3-thiadiazole-7-carbonyl)-1,2-diacetylhydrazine (Compound 6.7); 1-(benzo-1,2,3-thiadiazole-7-carbonyl )-2-phenylhydrazine (Compound 6.8); 1-(benzo-1,2,3-thiadiazole-7-carbonyl )-2-pyridin-2'-ylhydrazine (Compound 6.9).

Group B 2 (novel compounds)

7-n-pentoxycarbonylbenzo-1,2,3-thiadiazole (Compound 1.9); 7-(4-methoxybenzyloxycarbonyl)-benzo-1,2,3-thiadiazole (Compound 1.39); 7-(cyclohexumino-oxycarbonyl)-benzo-1,2,3-thiadiazole (Compound 1.72); 7-(3-hydroxy-n-propoxycarbonyl)-benzo-1,2,3-thiadiazole (Compound 1.79); 1,2,5,6-di-O-isopropylidene-3-(7-benzo-1,2,3-thiadiazoyl)-D-glucofuranose (Compound 1.86); 7-furfuryloxycarbonylbenzo-1,2,3-thiadiazole (Compound 1.96); 7-(1,2,4-triazol-1-yl)-methoxycarbonylbenzo-1,2,3-thiadiazole (Compound 1.100); 7-(2-pyridylmethoxycarbonyl)-benzo-1,2,3-thiadiazole (Compound 1.101); 7-trimethylsilylmethoxycarbonylbenzo-1,2,3-thiadiazole (Compound 1.103); 7-[2-(trimethylsilyl)-ethoxycarbonyl]-benzo-1,2,3-thiadiazole (Compound 1.104); 7-dimethylphosphonoethoxycarbonvlbenzo-1,2,3-thiadiazole (Compound 1.108); 7-cyclohexyloxycarbonylbenzo-1,2,3-thiadiazole (Compound 1.135); 7-(1-phenethyloxycarbonyl)-benzo-1,2,3-thiadiazole (Compound 1.140); 7-(3-methoxybenzyl)-benzo-1,2,3-thiadiazole (Compound 1.144);7-(ethylthiocarbonyl)-benzo-1,2,3-thiadiazole (Compound 2.2); 7-(n-propylthiocarbonyl)-benzo-1,2,3-thiadiazole (Compound 2.3); 7-(benzylthiocarbonyl)-benzo-1,2,3-thiadiazole (Compound 2.5); 7-carbamoylbenzo-1,2,3-thiadiazole (Compound 3.1); 7-N-phenylcarbamoylbenzo-1,2,3-thiadiazole (Compound 3.6); N-(7-benzo-1,2,3-thiadiazoyl)-glycine (Compound 3.9); 7-(N-diallylcarbamoyl)-benzo-1,2,3-thiadiazole (Compound 3.26); 6-fluoro-7-methoxycarbonylbenzo-1,2,3-thiadiazole (Compound 7.6); 6-fluoro-7-carboxybenzo-1,2,3-thiadiazole (Compound 7.8); 5-fluoro-7-benzyloxycarbonylbenzo-1,2,3-thiadiazole (Compound 7.52); 5-fluoro-7-carboxybenzo-1,2,3-thiadiazole (Compound 7.59); 5-fluoro-7-ethoxycarbonylbenzo-1,2,3-thiadiazole (Compound 7.61).

Surprisingly, it has now been found that the compounds of formula I, used in accordance with the invention, prevent healthy plants from being attacked by harmful microorganisms from the outset and thus protect the plants from the damage caused by such an attack. The great advantage of the method of treating plants according to the invention lies in the fact that instead of chemical substances acting directly on the plant-destructive microorganisms, the plant's own biological defence system is activated and stimulated before the plant is attacked, so that it can be ensured that the treated plants remain healthy by virtue of their own resources without any further direct use of microbicidal substances during the vegetative period. It is therefore especially characteristic of compounds of formula I that when they are used at environmentally safe application rates they do not act directly on the harmful organisms, but instead have an action immunising healthy plants against plant diseases. In this connection it was not possible to detect any direct action against members of the most important groups of fungi (for example *Fungi imperfecti,* Oomycetes). Accordingly, the use of the compounds of formula I according to the invention avoids disadvantageous side-effects, which otherwise are to be observed to a greater or lesser extent in the case of the direct control of parasites on plants by means of chemical substances, and this has the advantageous result that the growth of the plants is completely undisturbed. Furthermore, in the case of some of the novel compounds falling within the scope of formula I', a microbicidal, especially phytofungicidal, activity can occur in addition to and independently of the plant-immunising activity.

The mode of action of the compounds of formula I that underlies the invention has at the same time the aim of generally increasing the capacity of the treated plants to defend themselves, so that a general antimicrobial resistance to a broad spectrum of harmful microorganisms is thereby attained. The method according to the invention is therefore particularly suitable for practical uses. The systemic activity inherent in the compounds of formula I means that the protective action extends also to the parts of the treated plants that grow later.

The immunising method according to the invention is effective against phytopathogenic fungi belonging to the following classes: *Fungi imperfecti* (e.g. Botrytis, Helminthosporium, Fusarium, Septoria, Cercospora and Alternaria); Basidiomycetes (e.g. the genera Hemileia, Rhizoctonia, Puccinia); and Ascomycetes (e.g. Venturia, Podosphaera, Erysiphe, Monilinia, Uncinula).

The immunising method can be used especially advantageously against the following harmful organisms: fungi, for example Oomycetes (for example *Plasmopara viticola, Phytophthora infestans*), *Fungi imperfecti* (for example *Colletotrichum lagenarium, Piricularia oryzae, Cercospora nicotinae*), Ascomycetes (for example *Venturia inaequalis*); bacteria, for example pseudomonads (*Pseudomonas lachrymans, Pseudomonas tomato, Pseudomonas tabaci*); xanthomonads (for example *Xanthomonas oryzae, Xanthomonas vesicatoria*), Erwinia (for example *Erwinia amylovora*); and viruses, for example the tobacco mosaic virus.

The method according to the invention can be used for the protection of plants from different crops of useful plants.

Within the scope of the present invention the areas of indication disclosed herein apply e.g. to the following species of plants: cereals (wheat, barley, rye, oats, rice, sorghum and related crops), beet (sugar beet and fodder beet), pomes, drupes and soft fruit (apples, pears, plums, peaches, almonds, cherries, strawberries, raspberries and blackberries), leguminous plants (beans, lentils, peas, soybeans), oil plants (rape, mustard, poppy, olives, sunflowers, coconut, castor oil plants, cocoa beans, groundnuts), cucumber plants (cucumber, marrows, melons), fibre plants (cotton, flax, hemp, jute), citrus fruit (oranges, lemons, grapefruit, mandarins), vegetables (spinach, lettuce, asparagus, cabbages, carrots, onions, tomatoes, potatoes, paprika), *lauraceae* (avocados, cinnamon, camphor), or plants such as maize, tobacco, nuts, coffee, sugar cane, tea, vines, hops, bananas and natural rubber plants, as well as ornamentals (flowers, shrubs, deciduous trees and conifers).

This list does not constitute a limitation.

The following plants are to regarded as being particularly suitable target crops for the use of the method according to the invention: cucumbers, tobacco, vines, rice, cereals (for example wheat), pears, pepper, potatoes, tomatoes and apples.

The compounds of formula I can be prepared by the following processes:

1. compounds of formula Ia

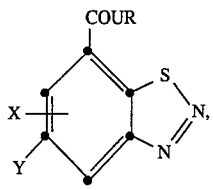

in which R, X, Y and U have the meanings given under formula I, are prepared by reacting:

1.1 compounds of formula II

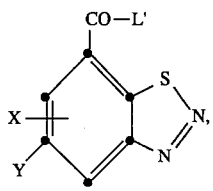

in which L' is a leaving group, for example halogen, O-acyl, for example the acyl radical belonging to the symmetric anhydride of acid Ib, or 1-imidazoyl,
with compounds of formula III

RUH    (III)

a) in an excess of the reactant RUH or b) in the presence of an organic base either with or without 4-dialkylaminopyridine as catalyst in inert solvents or c) in the presence of an inorganic base, the reaction in each case being carried out in a temperature range of from $-10°$ to $180°$ C., preferably from $0°$ to $100°$ C.; and 1.2 compounds of formula Ib

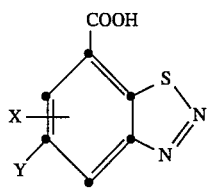

with compounds of formula III in excess or in an inert solvent in the presence of an acid, such as sulfuric acid, hydrochloric acid, p-toluenesulfonic acid or boron trifluoride/diethyl ether complex, or in the presence of dicyclohexylcarbodiimide at a temperature of from $-10°$ to $180°$ C., preferably from $0°$ to $140°$ C.; and 2. compounds of formula Ic

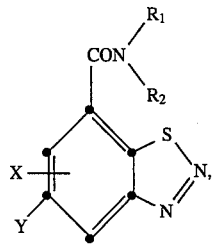

in which the symbols R1, R2, X and Y have the meanings given under formula I, are prepared by reacting:

2.1 compounds of formula II with compounds of formula IV

a) in an excess of the reactant $HN(R_1)R_2$ or b) in the presence of an organic base either with or without 4-dialkyl-aminopyridine as catalyst in inert solvents or c) in the presence of an inorganic base, the reaction in each case being carried out in a temperature range of from $-10°$ to $160°$ C., preferably from $0°$ to $100°$ C.; and 3. compounds of formula Id

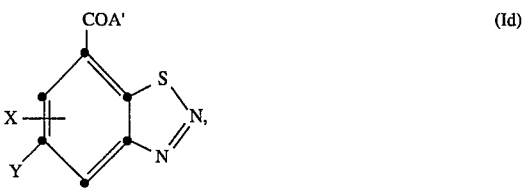

in which A' is the radical $U^1N(=C)_n(R_3)R_5$ and X, Y, R3, $R_3$, $R_5$ and n have the meanings given under formula I, are prepared by:

3.1 reacting compounds of formula Ie

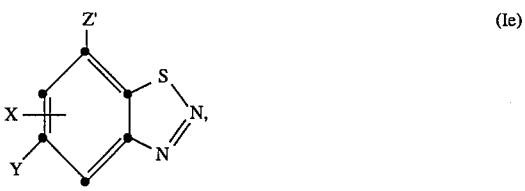

in which Z' is a group COOH, COCl, COOAlk$^1$ or an acyloxycarbonyl radical, for example

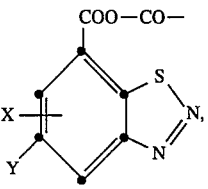

benzoyloxycarbonyl or acetoxycarbonyl, wherein Alk1 is $C_1$–$C_4$alkyl, in the presence of a base, with hydrazine derivatives of formula V or VI

in an inert solvent at a temperature of from $-10°$ to $180°$ C., preferably from $0°$ to $100°$ C.; or 3.2 reacting compounds of formula Ie stepwise first with hydrazine, and then reacting the resulting hydrazine compounds 3.2.1 with the alkylating agent $R_3$-L or $R_4$-L in which L is a leaving group, in an inert solvent at a temperature of from $0°$ to $160°$ C., preferably from $20°$ to $120°$ C.; or 3.2.2 with an aldehyde or ketone of formula $R_3(R_4)C=O$ in which $R_3$ and $R_4$ have the meanings given under formula I, with or without the addition of an organic or inorganic acid, at a temperature of from −10° to 150° C., preferably from 20° to 100° C., and subsequently, if desired, 3.2.3 with an alkylating agent $L-R_5$ in which L is a leaving group, in the presence of a strong base in an inert solvent at a temperature of from −80° to 120° C., preferably from −40° to 80° C.; or, if desired, 3.2.4 a) hydrogenating the hydrazone derivatives prepared under (3.2.1) with hydrogen at a pressure of from 1 to $30 \times 10^5$ Pa in the presence of a catalyst in admixture with activated carbon in an inert solvent at a temperature of from 0° to 100° C., or 3.2.4 b) treating the hydrazone derivatives prepared under (3.2.1) with a complex metal hydride, for example sodium cyanoborohydride, in an inert solvent at a temperature of from −10° to 80° C., preferably from 0° to 50° C.; and 4. compounds of formula If

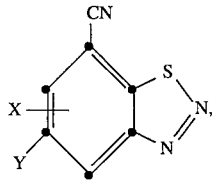

(If)

in which the symbols X and Y have the meanings given under formula I, are prepared by treating compounds of formula Ig [prepared according to process (2)]

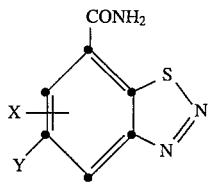

(Ig)

with a dehydrating agent in an inert solvent or without a solvent at a temperature of from −10° to 250° C., suitable dehydrating agents being:

a) trifluoroacetic acid anhydride in the presence of a base, for example pyridine, in an inert solvent, for example tetrahydrofuran or dioxane, at a temperature of from −10° to 40° C.; or b) chlorosulfonyl isocyanate in an inert solvent, for example tetrahydrofuran, at a temperature of from 0° to 65° C., with subsequent treatment with dimethylformamide (see Org. Synth. 50, 18 or Chem. Ber. 100, 2719); or c) phosphorus pentoxide with or without an inert solvent, for example 1,2-dichloroethane, xylene or chlorobenzene, optionally in a bomb tube under elevated pressure, at from 50° to 250° C. (see Fieser, Reagents for Organic Synthesis !, 871);

5.1 compounds of formula $IL^1$

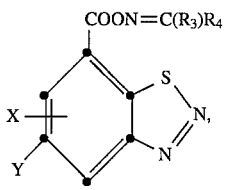

($IL^{1)}$)

in which $R_3$, $R_4$, X and Y have the meanings given under formula I, are prepared by reacting oxime derivatives of formula

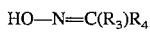

with activated acid derivatives of formula

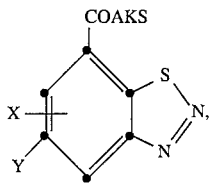

in which AKS is a halogen, an O-acyl, for example the O-acyl radical of the free acid of the formula above, acetoxy or benzoyloxy, or 1-imidazolyl, in an inert solvent and a base at from −20° C. to 120° C., preferably from 0° to 50° C., or by reacting the free acid (=Ib) in the presence of dicyclohexylcarbodiimide under the same conditions (Lit. Bet. 83, 186 (1950); Houben-Weyl ES, p. 773);

5.2 compounds of formula $IL^2$

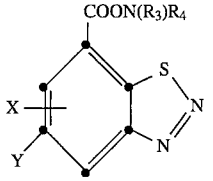

($IL^{2)}$)

in which $R_3$, $R_4$, X and Y have the meanings given under formula I, are prepared by reduction of compounds of formula $IL^1$

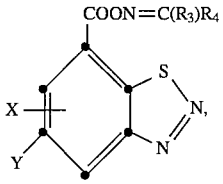

($IL^{1)}$)

a) with a silane, for example triethylsilane, in the presence of an acid, for example trifluoroacetic acid, at from 0° to 80° C., or b) with sodium cyanoborohydride in the presence of an organic acid, for example acetic acid, at from 0° to 80° C., or c) by catalytic methods, for example with $Pt/H_2$.

In a special synthesis method, compounds of formula $IL^2$ in which $R_3$ and $R_4$ are hydrogen are prepared by reacting an acid halide or an acid anhydride of an acid of formula Ib

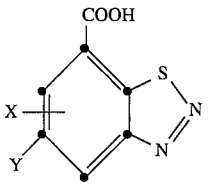

(Ib)

with N,O-bis-trimethylsilylhydroxylamine in the presence of a base, for example butyllithium, in an inert solvent at from −80° to 60° C., preferably from −50° to 50° C.

The 7-carboxylic acid esters described in the above formulae in which U is oxygen and R has the meanings given under formula I, provided they are not radicals that contain OH groups or silicon- or phosphorus-containing groups, can be converted into one another according to transesterification methods described in the literature.

The precursor compounds of formulae Ib, Ie and II can be prepared according to known methods, for example within the scope of the following synthesis:

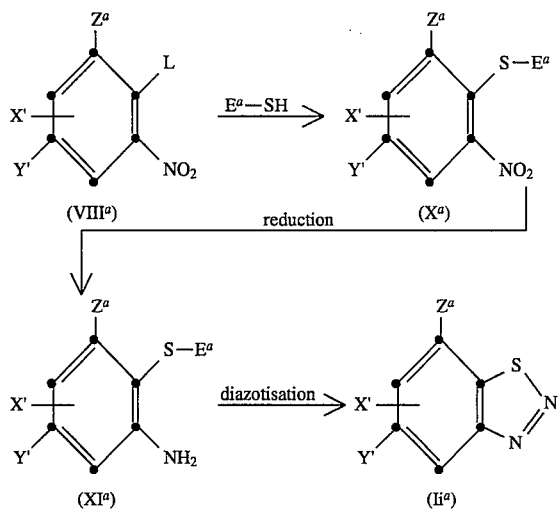

in which Y' is hydrogen, halogen, SO$_3$H, SO$_3$M or hydroxy; X' is hydrogen, halogen, methyl, methoxy or COOH; E$^a$ is a readily removable group, for example hydrogen or C$_1$–C$_4$alkyl, for example methyl, ethyl or isopropyl, or benzyl; L is halogen or nitro; Z$^a$ is a group COOH or COOC$_1$–C$_4$alkyl.

If Z$^a$ is a free acid group (—COOH), this group can be converted using customary methods into an ester group, for example the methyl ester, into an acid halide, for example the acid chloride, or into the symmetric or a mixed acid anhydride, for example with the acetyl or benzoyl radical.

In a parallel method of synthesis there are prepared those compounds of formula I represented by formula I'$^b$

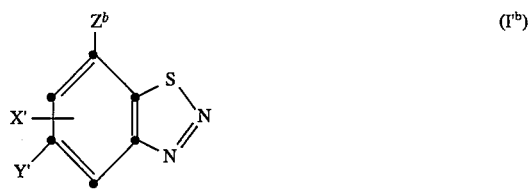
(I'$^b$)

in which Z$^b$ has the meanings of Z given under formula I provided they are not radicals that contain primary amino or secondary amino groups, UH or nitro groups, Si(C$_1$–C$_8$alkyl)$_3$ or phosphorus-containing groups, and X' and Y' have the meanings given above under formula Ii$^a$.

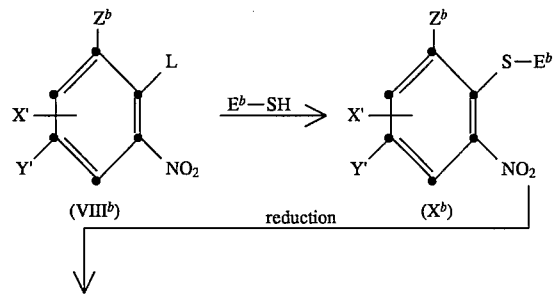

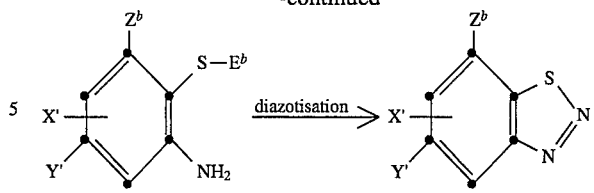

in which E$^b$ is a readily removable group, for example hydrogen, C$_1$–C$_{16}$-alkyl, for example methyl, ethyl, isopropyl, n-dodecyl, or benzyl or acyl, for example acetyl or the sulfonic acid radical (—SO$_3$H—) or cyano, or as part of a disulfide bridge, is a second radical

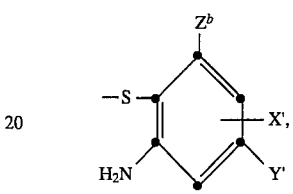

and L has the meaning given under formula VIII$^a$.

Furthermore, compounds of formula Ik

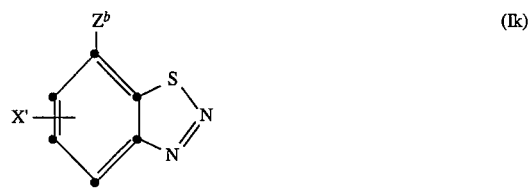
(Ik)

can be prepared according to a special process (C) by diazotisation of a compound of formula XI'

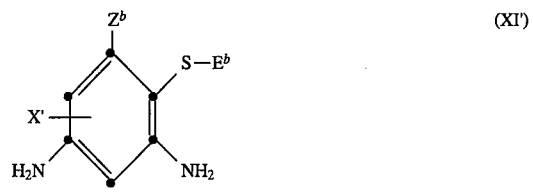
(XI')

in which X', E$^b$ and Z$^b$ have the meanings given above under formula XI', in an acidic medium with a nitrite compound at from −40° to 30° C., and in the same reaction vessel or in a second reaction vessel treatment with a reducing agent at from −40° to 80° C., preferably from -30° to 30° C., it being possible to add the reducing agent before, after or at the same time as the nitrite compound.

In a special form of process (C), Z$^b$ in the above formulae XI' and Ik is an acid ester (COOR$^a$), X' is hydrogen and Ra has the same meanings as R with the exception of radicals containing UH or nitro groups and of silicon- or phosphorus-containing radicals, compounds of formula

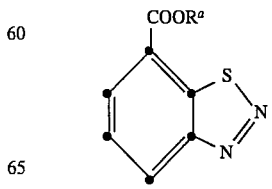

being prepared by diazotisation of a compound of formula

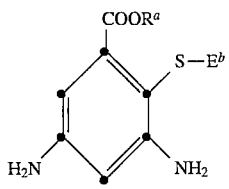

in an acidic medium with a nitrite compound at a temperature of from −20° to 30° C., and in the same reaction vessel reduction at a temperature of from −20° to 80° C., preferably from 20° to 30° C., it being possible to add the reducing agent before, after or at the same time as the nitrite compound.

Using a further special process it is possible to prepare compounds of formula Ik'

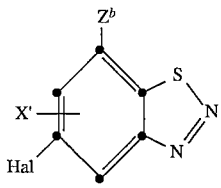

by diazotisation of a compound of formula XI'

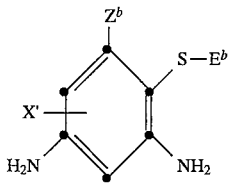

in which X', $E^b$ and $Z^b$ have the meanings given above under formula XI', in an acidic medium with a nitrite compound at from −40° to 30° C., and a) reaction of the diazonium salt with a copper halide at a temperature of from −30° to 180° C., or b) if Hal is fluorine, treatment of the diazonium salt with hydrofluoric acid or tetrafluoroboric acid, optionally in the presence of copper fluoride salts (Lit. Houben-Weyl, 5/3, 216).

In process (C) described above, the acidic reaction medium used may be an aqueous dilution of an inorganic acid, such as, for example, a hydrohalic acid, phosphoric acid, sulfuric acid or hydrofluoroboric acid; it is, however, also possible to use suitable organic acids, to which inert organic solvents, for example tetrahydrofuran or dioxane, may be added. Suitable nitrites are both inorganic nitrite compounds, for example the alkali metal and alkaline earth metal salts, and organic nitrite compounds, for example alkyl nitrites. Reducing agents may be, for example, alcohols, for example ethanol, or hypophosporous acid, metallic copper or trialkylsilanes, for example triethylsilane, and ferrocyanides or ferrocenes, for example decamethylferrocene. The reduction step can, if desired, be carried out in the presence of further additives, for example Crown ethers or polyethylene glycol.

The described method (C) is a novel process of a chemically unique nature with which it is possible to obtain fused thiadiazole compounds in an advantageous manner.

The synthesis of the precursors of compound XI'

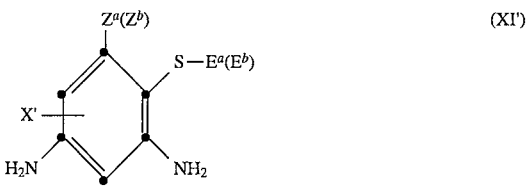

is carried out by reacting compounds of formulae VIII', VIII" and IX

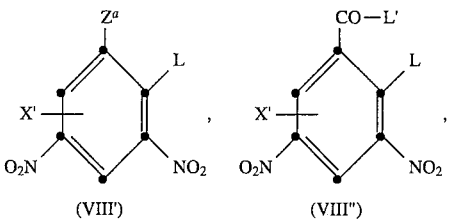

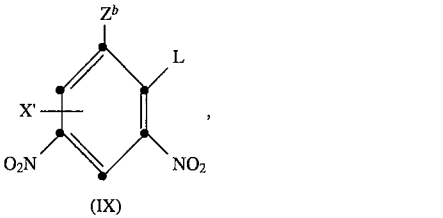

in which formulae the substituents have the following meanings: X' is hydrogen, halogen, methyl, methoxy or COOH; $E^a$ is a readily removable group, for example hydrogen, $C_1$–$C_4$alkyl, for example methyl, ethyl or isopropyl, or benzyl; $E^b$ is a readily removable group, for example hydrogen, $C_1$–$C_6$alkyl, for example methyl, ethyl, isopropyl, n-dodecyl, or benzyl or acyl, for example acetyl or the sulfonic acid radical (—$SO_3H$—) or cyano or, as part of a disulfide bridge, is a second radical

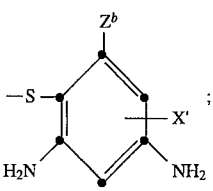

L is halogen or nitro; L' is a leaving group, for example halogen, O-acyl, for example the acyl radical belonging to the symmetric anhydride of the acid Ib, or 1-imidazoyl; $Z^a$ is a group COOH or COO$C_1$–$C_4$alkyl; $Z^b$ has the meanings of Z given under formula I provided they are not radicals that contain primary or secondary amino groups, nitro or UH groups, Si($C_1$–$C_8$alkyl)$_3$ or phosphorus-containing groups; with compounds of the formulae HS-$E^a$ or HS-$E^b$ in the presence of a base, for example an alkali metal carbonate (for example $Na_2CO_3$ or $K_2CO_3$) or an alkaline earth metal carbonate (for example $MgCO_3$), alkoxides (for example sodium alcoholates or potassium tert.-butoxide), or alkali metal hydrides (for example sodium hydride), in an inert, preferably dipolar aprotic solvent {for example dimethyl sulfoxide, dimethylformamide, hexamethylphosphoric acid triamide, N-methylpyrrolidone, acetonitrile, dioxane or tetrahydrofuran) at a temperature of from −10° to 120° C., preferably from 0° to 60° C., to form compounds of formula X'

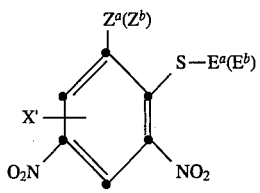

which are converted into the compounds of formula XI'

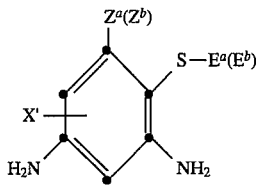

by either catalytic or metallic reduction.

For the catalytic reduction it is possible to use, for example, Raney nickel and palladium, platinum or rhodium catalysts; the reduction can be carried out under normal pressure or slightly elevated pressure at a temperature of from 0° to 150° C. Suitable solvents are, for example, tetrahydrofuran or dioxane.

For the metallic reduction it is possible to use, for example, iron/hydrochloric acid, iron/acetic acid, tin/hydrochloric acid, zinc/hydrochloric acid, zinc/acetic acid, copper/formic acid.

Further suitable reducing agents are tin(II) chloride/hydrochloric acid, nickel/hydrazine, titanium trichloride, alkali metal sulfides or sodium dithionite. The reduction can be carried out at a temperature of from 0° to 120° C., and water or alcohols, for example methanol, ethanol, n-propanol or isopropanol, can be used as solvents.

Furthermore, if $Z^a$ is the acid function (—COOH), it is possible to prepare special derivatives of formula IX in which $Z^b$ is a radical —COUR'—, —CON($R_1$)$R_2$ or —CON($R_5$)N($R_3$)$R_4$, by a) reacting, in a known manner, the derivative of formula VIII$^a$ (Y'=NO$_2$) synthesised first, with an alcohol of formula HUR' or an amine of formula HN($R_1$)$R_2$ or with a hydrazide of formula HN($R_5$)N($R_3$)$R_4$ in the presence of a suitable base, optionally catalysed by the addition of dimethylaminopyridine, in an inert solvent at a temperature of from −20° to 170° C., preferably from 0° to 110° C., or b) reacting a compound of formula VIII' ($Z^a$=COOH) in the presence of dicyclohexylcarbodiimide with an alcohol of formula HUR' or with an amine of the formula HN($R_1$)$R_2$ or with a hydrazide of formula HN($R_5$)N($R_3$)$R_4$ in an inert solvent at a temperature of from 0° to 120° C., preferably from 10° to 80° C.

The meanings of the radicals $R_1$ to $R_5$ and the symbol U have already been described in the text above and R' has the same meaning as R with the exception of the radicals (T)-P(O)(OR$_6$)-(C$_1$-C$_4$alkyl), (T)-PO(OR$_6$)$_2$ and (T)$_n$-Si(C$_1$-C$_6$alkyl)$_3$.

The compounds of formula XI' are novel and form part of the present invention:

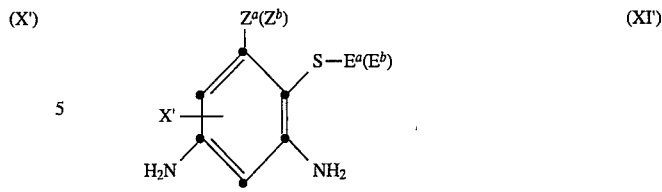

wherein X' is hydrogen, halogen, methyl, methoxy or COOH; $E^a$ is a readily removable group, for example hydrogen, C$_1$-C$_4$alkyl, for example methyl, ethyl or isopropyl, or benzyl; $E^b$ is a readily removable group, for example hydrogen, C$_1$-C$_{16}$alkyl, for example methyl, ethyl, isopropyl, n-dodecyl, or benzyl or acyl, for example acetyl or the sulfonic acid radical (—SO$_3$H—) or cyano or, as part of a disulfide bridge, is a second radical

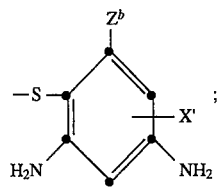

$Z^a$ a group COOH or COOC$_1$-C$_4$alkyl; $Z^b$ has the meanings of Z given under formula I provided they are not radicals that contain primary or secondary amino groups, UH or nitro groups, Si(C$_1$-C$_8$alkyl)$_3$ or phosphorus-containing groups.

Compounds of formula XI' have microbicidal activity, especially against phytopathogenic fungi and bacteria.

The compounds of formula X' are known or can be prepared according to processes known in the literature. Some of these derivatives can be prepared in accordance with a special process as follows:

Compounds of formula

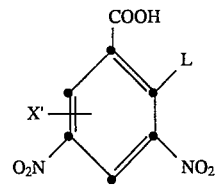

are first reacted in the presence of 2 equivalents of a base, for example an alkali metal carbonate (for example NarCO$_3$ or K$_2$CO$_3$) or an alkaline earth metal carbonate (for example MgCO$_3$) or a metal hydride (for example NaH or LiH) with a compound of formula HS-E$^a$ or HS-E$^b$ in an inert, preferably dipolar aprotic solvent, for example dimethyl sulfoxide, dimethylformamide, hexamethylphosphonic acid triamide or N-methylpyrrolidone, and the resulting derivative is esterified with an alkylating agent R$^a$-L" in which L" is a leaving group, for example halogen, preferably iodine, or —OSO$_2$R$^a$ in which R$^a$-L" can be, for example, dimethyl sulfate:

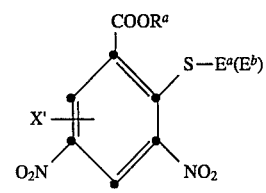

In the above formulae, R$^a$ is an aliphatic or araliphatic radical defined under R for formula I and the radicals L, S-E$^a$ S-E$^b$ and X' have the meanings given under formulae VIII', VIII" and IX.

In the processes described above, unless indicated otherwise bases are to be understood as being both inorganic and organic bases. These include, as inorganic bases, for example, hydroxides, hydrogen carbonates, carbonates and hydrides of lithium, sodium, potassium, calcium and barium, and alkali metal amides, for example NaNH$_2$ or alkyllithium compounds, for example n-butyllithium. Examples of organic bases that may be mentioned are: amines, especially tertiary amines, for example trimethylamine, triethylamine, tripropylamine, tributylamine, tribenzylamine, tricyclohexylamine, triamylamine, trihexylamine, N,N-dimethylaniline, N,N-dimethyltoluidine, N,N-dimethyl-p-aminopyridine, N-methylpyrrolidine, N-methylpiperidine, N-methylpyrrolidine, N-methylimidazole, N-methylpyrrole, N-methylmorpholine, N-methylhexamethyleneimine, pyridine, quinoline, α-picoline, β-picoline, isoquinoline, pyrimidine, acridine, N,N,N',N'-tetramethylethylenediamine, N,N,N',N'-tetraethylethylenediamine, quinoxaline, N-propyldiisopropylamine, N,N-dimethylcyclohexylamine, 2,6-lutidine, 2,4-lutidine or triethylenediamine.

Examples of inert solvents that may be used in accordance with the particular reaction conditions are:

halogenated hydrocarbons, especially chlorinated hydrocarbons, for example tetrachloroethylene, tetrachloroethane, dichloropropane, methylene chloride, dichlorobutane, chloroform, chloronaphthalene, dichloronaphthalene, carbon tetrachloride, trichloroethane, trichloroethylene, pentachloroethane, difluorobenzene, 1,2-dichloroethane, 1,1-dichloroethane, 1,2-cis-dichloroethylene, chlorobenzene, fluorobenzene, bromobenzene, iodobenzene, dichlorobenzene, dibromobenzene, chlorotoluene, trichlorobenzene; ethers, for example ethyl propyl ether, methyl tert.-butyl ether, n-butyl ethyl ether, di-n-butyl ether, diisobutyl ether, diisoamyl ether, diisopropyl ether, anisole, phenetol, cyclohexyl methyl ether, diethyl ether, ethylene glycol dimethyl ether, tetrahydrofuran, dioxane, thioanisole, dichlorodiethyl ether, methylcellosolve; alcohols, for example methanol, ethanol, n-propanol, isopropanol, n-butanol, isobutanol nitrohydrocarbons, for example nitromethane, nitroethane, nitrobenzene, chloronitrobenzene, o-nitrotoluene; nitriles, for example acetonitrile, butyronitrile, isobutyronitrile, benzonitrile, m-chlorobenzonitrile; aliphatic or cycloaliphatic hydrocarbons, for example heptane, pinane, nonane, cymol, petroleum fractions within a boiling point range of from 70° to 190° C., cyclohexane, methylcyclohexane, decalin, petroleum ether, hexane, ligroin, trimethylpentane, trimethylpentane, 2,3,3-trimethylpentane, octane; esters for example ethyl acetate, acetoacetic acid esters, isobutyl acetate; amides, for example formamide, methylformamide, dimethylformamide; ketones, such as acetone, methyl ethyl ketone, and optionally also water. Mixtures of the mentioned solvents and diluents are also suitable.

The preparation methods described above, where they are not novel, are based on known synthesis methods that can be found in the following literature:

The Chemistry of Heterocyclic Compounds with Nitrogen and Sulfur or Nitrogen, Sulfur and Oxygen, Interscience Publ., New York 1952; P. Kirby et al., J. Chem. Soc. (C) 321 (1967) and 2250 (1970) and 3994 (1971); FR-PS 1 541 415; J. Org. Chem. 27, 4675 (1962); German Offenlegungsschriften Nos. 2 400 887 and 2 504 383; SU-PS 400 574 [Chem. Abstr. 80(9)47661 hi; Org. Synth. Coll. Vol. I, 125; Tetrahedr. 21, 663 (1965).

The compounds of formulae X, X', XI and XI' are novel substances, whilst some of the compounds of formulae VIII, VIII' and IX are novel. The novel compounds form part of the present invention.

The plant-protective compositions used within the scope of the invention which contain compounds of formula I as active ingredients are likewise to be regarded as forming part of the invention.

The compounds of formula I are normally applied in the form of compositions and can be applied to the plant or to the locus thereof, simultaneously or in succession, with further compounds. These compounds can be fertilisers or micronutrient donors or other preparations that influence plant growth. They can also be selective herbicides, insecticides, fungicides, bactericides, nematicides, molluscicides or mixtures of several of these preparations, if desired together with further carriers, surfactants or application-promoting adjuvants customarily employed in the art of formulation.

Suitable carriers and adjuvants can be solid or liquid and correspond to the substances ordinarily employed in formulation technology, e.g. natural or regenerated mineral substances, solvents, dispersants, wetting agents, tackifiers, thickeners, binders or fertilisers.

A preferred method of applying a compound of formula I, or an agrochemical composition which contains at least one of said compounds, is foliar application. However, the compounds of formula I can also penetrate the plant through the roots via the soil (systemic action) if the locus of the plant is impregnated with a liquid formulation, or if the compounds are applied in solid form to the soil, e.g. in granular form (soil application). The compounds of formula I may, however, also be applied to seeds (coating) by impregnating the seeds either with a liquid formulation containing a compound of formula I, or coating them with a solid formulation (dressing). Furthermore, in some cases other methods of application may be possible, for example the specific treatment of the plant stem or buds.

The compounds of formula I are used in unmodified form or, preferably, together with the adjuvants conventionally employed in the art of formulation, and are for this purpose formulated in known manner e.g. into emulsifiable concentrates, coatable pastes, directly sprayable or dilutable solutions, dilute emulsions, wettable powders, soluble powders, dusts, granulates, and also encapsulations in e.g. polymer substances. As with the nature of the compositions, the methods of application, such as spraying, atomising, dusting, scattering, coating or pouring, are chosen in accordance with the intended objectives and the prevailing circumstances. Advantageous rates of application are normally from 50 g to 5 kg of active ingredient (a.i.) per hectare, preferably from 100 g to 2 kg a.i./ha, most preferably from 100 g to 600 g a.i./ha.

The formulations, i.e. the compositions, preparations or mixtures containing the compound (active ingredient) of formula I and, where appropriate, a solid or liquid adjuvant, are prepared by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethyl sulfoxide or dimethylformamide, as well as vegetable oils or epoxidised vegetable oils, such as epoxidised coconut oil or soybean oil; or water.

The solid carriers used e.g. for dusts and dispersible powders, are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable nonsorbent carriers are, for example, calcite or sand. In addition, a great number of pregranulated materials of inorganic or organic nature can be used, e.g. especially dolomite or pulverised plant residues. Particularly advantageous application-promoting adjuvants are also natural (animal or vegetable) or synthetic phospholipids of the series of the cephalins and lecithins.

Depending on the nature of the compound of formula I to be formulated, suitable surface-active compounds are non-ionic, cationic and/or anionic surfactants having good emulsifying, dispersing and wetting properties. The term "surfactants" will also be understood as comprising mixtures of surfactants.

Cationic surfactants are preferably quaternary ammonium salts which contain, as N-substituent, at least one $C_8$–$C_2$alkyl radical and, as further substituents, unsubstituted or halogenated lower alkyl, benzyl or hydroxy-lower alkyl radicals.

Both so-called water-soluble soaps and also water-soluble synthetic surface-active compounds are suitable anionic surfactants.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid or of natural fatty acid mixtures which can be obtained e.g. from coconut oil or tallow oil.

Synthetic surfactants that may be used are especially fatty alcohol sulfonates, fatty alcohol sulfates, sulfonated benzimidazole derivatives or alkylsulfonates. The fatty alcohol sulfonates or sulfates are usually in the form of alkali metal salts, alkaline earth metal salts or unsubstituted or substituted ammonium salts and contain a $C_8$–$C_{22}$alkali radical.

Non-ionic surfactants are preferably polyglycol ether derivatives of aliphatic or cycloaliphatic alcohols, saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

The compositions may also contain further auxiliaries such as stabilisers, antifoams, viscosity regulators, binders, tackifiers as well as fertilisers or other active ingredients for obtaining special effects.

The agrochemical compositions usually contain 0.1 to 99% by weight, preferably 0.1 to 95% by weight, of a compound of formula I, 99.9 to 1% by weight, preferably 99.8 to 5% by weight, of a solid or liquid adjuvant, and 0 to 25% by weight, preferably 0.1 to 25% by weight, of a surfactant.

The Examples which follow serve to illustrate the invention in more detail but do not constitute a limitation thereof.

1. Preparation Examples

Example 1.1: Preparation of 2-chloro-3-nitrobenzoic acid methyl ester (intermediate)

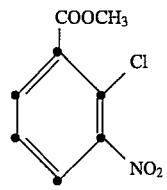

50.0 g (0.248 mol) of 2-chloro-3-nitrobenzoic acid are dissolved in 500 ml of methanol, and 20 ml of concentrated sulfuric acid are added thereto. After refluxing for 24 hours, the mixture is poured onto ice/water and the white precipitate is isolated by filtration, washed with water and dried. Yield: 53 g (99 % of the theoretical yield); m.p. 68° C.

Example 1.2: Preparation of 2-benzylthio-3-nitrobenzoic acid methyl ester (intermediate)

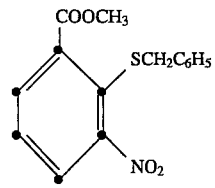

45.4 g (0.21 mol) of 2-chloro-3-nitrobenzoic acid methyl ester and 24.8 ml (0.21 mol) of benzyl mercaptan are dissolved in 420 ml of dimethylformamide, and then 29.2 g (0.21 mol) of potassium carbonate are added and the batch is stirred for 8 hours at 80° C. It is then poured onto ice/water and extracted twice with ethyl acetate. The extracts are washed with water, dried over magnesium sulfate and concentrated by evaporation. Yield: 62.7 g (98.5 % of the theoretical yield) oil.

Example 1.3: Preparation of 3-amino-2-benzylthiobenzoic acid methyl ester (intermediate)

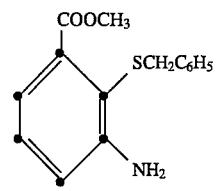

62.7 g (0.207 mol) of 2-benzylthio-3-nitrobenzoic acid methyl ester are dissolved in 700 ml of tetrahydrofuran, 14 g of Raney nickel are added and the batch is hydrogenated at 20°–28° C. Yield: 54.5 g (96 % of the theoretical yield).

Example 1.4: Preparation of 5-bromo-2-chloro-3-nitrobenzoic acid methyl ester (intermediate)

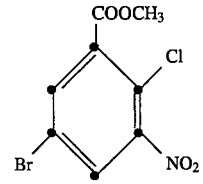

20 ml of concentrated sulfuric acid are added dropwise to 51.0 g (0.182 mol) of 5-bromo-2-chloro-3-nitrobenzoic acid and 500 ml of methanol. The mixture is then boiled under reflux for 16 hours and subsequently cooled with an ice bath and the resulting precipitate is isolated by filtration. The mother liquor is concentrated, water is added and the resulting precipitate is isolated by filtration. Yield: 50.2 g (94 % of the theoretical yield), m.p. 69° C.

Example 1.5: Preparation of 2-benzylmercapto-5-bromo-3-nitrobenzoic acid methyl ester (intermediate)

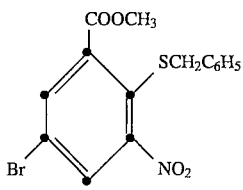

71.6 g (0.58 mol) of benzyl mercaptan are dissolved in 2.9 l of methanol/water (8:2), and 79.8 g (0.58 mol) of potassium carbonate are added. At 0°–5° C., 170 g (0.58 mol) of 5-bromo-2-chloro-3-nitrobenzoic acid methyl ester are added in portions over a period of 2.5 hours with stirring. Stirring is then continued for a further 2 hours and the internal temperature is then raised to 20° C. The resulting precipitate is then isolated by filtration, washed with a small amount of water and subsequently with 500 ml of methanol/water. After drying, 208 g (94%) of pale yellow product are obtained. Recrystallisation from 400 ml of methanol gives 190 g (86% of the theoretical yield) of product having a melting point of 65°–660° C.

Example 1.6: Preparation of 3-amino-2-benzylthiobenzoic acid methyl ester (intermediate)

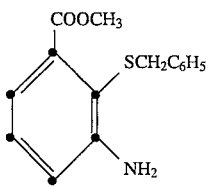

156.25 g (0.408 mol) of 2-benzylthio-5-bromo-3-nitrobenzoic acid methyl ester are hydrogenated in 3 l of tetrahydrofuran in the presence of 60 g of Pd/C (5%). After the reduction of the nitro group, a further 30 g of Pd/C (5%) and 45.4 g (0.448 mol) of triethylamine are added and hydrogenation is continued. The catalyst is then isolated by filtration and the solution is concentrated. The oily residue is taken up in ethyl acetate, washed three times with water, dried over magnesium sulfate and filtered, and the solution is concentrated by evaporation. The resulting product (111 g) is further processed directly.

Example 1.7: Preparation of 7-methoxycarbonylbenzo-1,2,3-thiadiazole

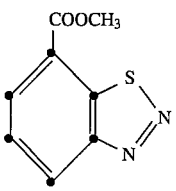

475 g (1.74 mol) of 3-amino-2-benzylthiobenzoic acid methyl ester are slowly added at 35° C. to 1.18 l of concentrated hydrochloric acid in 520 ml of water to form the hydrochloride. The batch is stirred for 15 minutes at that same temperature and is then cooled to −5° C. A solution of 120 g of sodium nitrite in 520 ml of water is then added dropwise over a period of 2.5 hours. When the dropwise addition is complete, the batch is stirred for 2 hours at 0° and for a further 2 hours at 20° C. The reaction material is isolated by filtration, washed with water and pressed off. Recrystallisation from ethyl acetate/hexane gives 292 g (86% of the theoretical yield) of product having a melting point of 134°–135° C.

Example 1.8: Preparation of benzo-1,2,3-thiadiazole-7-carboxylic acid

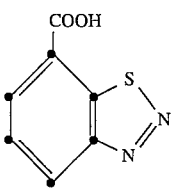

100 g (0.51 mol) of 7-methoxycarbonylbenzo-1,2,3-thiadiazole are suspended in 1000 ml of water, and then 310 ml of 2N sodium hydroxide solution and 5 ml of dioxane are added. The reaction mixture is heated to 40° C., is stirred for 4 hours at that temperature and is then cooled to 10° C. A further 1000 ml of water are added and the batch is neutralised with 310 ml of 2N hydrochloric acid. The resulting precipitate is isolated by filtration, lightly dried in a current of air and then dissolved in tetrahydrofuran and the solution is dried over magnesium sulfate, filtered and concentrated. The crystals are suspended in hexane, isolated by filtration and dried. Yield: 91 g (98 % of the theoretical yield); m.p. 261°–263° C.

Example 1.9a: Preparation of benzo-1,2,3-thiadiazole-7-carboxylic acid chloride (intermediate)

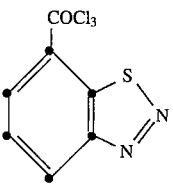

12.54 g (0.070 mol) of benzo-1,2,3-thiadiazole-7-carboxylic acid are mixed with 80 ml of thionyl chloride. The mixture is heated and maintained at a bath temperature of 90° C. for 8 hours. The excess thionyl chloride is then removed by distillation in a rotary evaporator at a bath temperature of 40° C. The resulting oil solidifies; m.p. 107° C.

For further reactions, the acid chloride obtained is dissolved in toluene and used further directly.

Example 1.9b: Preparation of the symmetrical anhydride of 1,2,3-benzothiadiazole-7-carboxylic acid

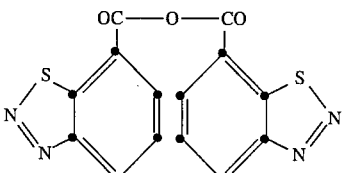

3 g of 1,2,3-benzothiadiazole-7-carboxylic acid are boiled under reflux in 50 ml of acetic anhydride for 24 hours. The thin suspension is then concentrated by evaporation in vacuo, and the solid residue is suspended in ether and isolated by filtration to give 4.3 g of anhydride having a melting point of 117°–119° C. The same compound is also obtained, for example, by heating the carboxylic acid with bis-(2-oxo-3-oxazolidinyl)phosphinic acid chloride in dry tetrahydrofuran (see Synthesis 1981, 616).

Example 1.10: Preparation of 7-cyanobenzo-1,2,3,-thiadiazole

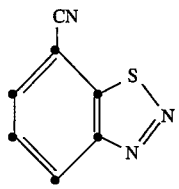

4.0 g (0.022 mol) of benzo-1,2,3-thiadiazol-7-ylcarboxylic acid amide are dissolved in 35 ml of tetrahydrofuran, and 3.6 ml (0.045 mol) of pyridine are added. The batch is then cooled to 3° C. and a solution of 3.9 ml (0.028 mol) of trifluoroacetic acid anhydride in 12 ml of tetrahydrofuran is added dropwise. The reaction mixture is subsequently stirred for 22 hours at room temperature and then poured onto ice/water and extracted twice with ethyl acetate. The extracts are washed with water, dried over magnesium sulfate and filtered through a layer of silica gel. Concentration by evaporation gives 3.5 g (99% of the theoretical yield) of crystalline product having a melting point of 119°–122° C.

Example 1.11: Preparation of benzo-1,2,3-thiadiazole-7-carboxylic acid hydrazide

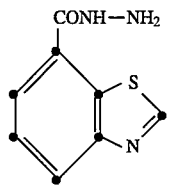

9.7 g of 7-methoxycarbonylbenzo-1,2,3-thiadiazole are reacted for 19 hours with 4.8 g of hydrazine hydrate in 30 ml of water at 50° C. and then for a further 6 hours at 80°–90° C. The suspension is cooled slightly, filtered while hot and washed with water to give 8.8 g of white crystals having a melting point of 270°–272° C.

Example 1.12: Preparation of 2-(benzo-1,2,3-thiadiazole-7-carbonyl)-1-(α-methylpropylidene)-hydrazine

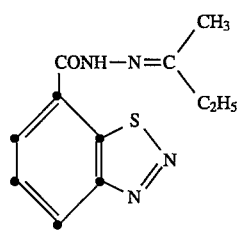

21.5 g of benzothiadiazole-7-carboxylic acid hydrazide and 150 ml of methyl ethyl ketone are heated to 70° C. over a period of 8 hours in 150 ml of glacial acetic acid. The reaction mixture is then concentrated by evaporation in vacuo, the residue is taken up in 1 l of dichloromethane and the solution is washed twice with 700 ml of ice/water. It is then dried over sodium sulfate, filtered and concentrated by evaporation and the residue is suspended in ethyl acetate, filtered and dried. The product indicated above melts at 159°–162° C.

Example 1.13: Preparation of 2-(benzo-1,2,3-thiadiazole-7-carbonyl)-1-( 2'-n-butyl)-hydrazine

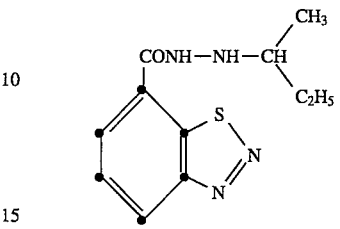

10.5 g of 2-(benzo-1,2,3-thiadiazole-7-carbonyl)-1-(α-methylpropylidene) hydrazine are dissolved in 150 ml of dimethylformamide and 100 ml of methylcellosolve and the solution is hydrogenated over 7 g of platinum/carbon at room temperature and at normal pressure. The catalyst is then isolated by filtration and the product that remains after concentrating the filtrate by evaporation is chromatographed with ethyl acetate on silica gel to give the product in the form of white crystals having a melting point of 148°–150° C.

Example 1.14: Preparation of 2-benzylthio-3,5-dinitrobenzoic acid methyl ester (intermediate)

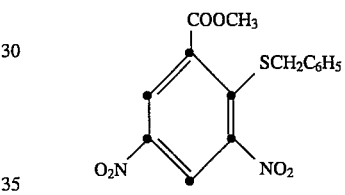

332 g (2.40 mol) of potassium carbonate are introduced into 500 ml of dimethylformamide and cooled to −5° C. 375 g (1.14 mol) of 2-chloro-3,5dinitrobenzoic acid (75% with 25% water; transport and storage form) in 1.1 l of dimethylformamide are then added over a period of 30 minutes, during which time the internal temperature is maintained at from −5° to 4° C. 142 g (1.14 mol) of benzyl mercaptan are then added dropwise at from 0° to 3° C. over a period of 2.5 hours. The temperature is subsequently raised to 20° C. over a period of 16 hours. 170 g (1.2 mol) of methyl iodide are then added dropwise at room temperature over a period of 5 hours. The reaction mixture is then stirred for 16 hours at room temperature and afterwards poured onto 3 l of ice/water, stirred and filtered. The material obtained by filtering with suction is washed four times with 700 ml of water each time and is hydrogenated in the next stage while still damp (see Example 1.15). The dried product has a melting point of 113°–114° C.

Example 1.15: Preparation of 2-benzylthio-3,5-diaminobenzoic acid methyl ester (intermediate)

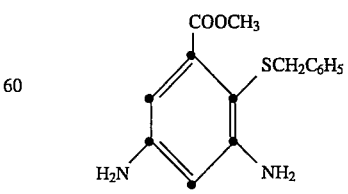

The 2-benzylthio-3,5-dinitrobenzoic acid methyl ester obtained in the previous stage (see Example 1.14), which is still damp, is dissolved in 2 l of tetrahydrofuran and hydrogenated at from 30° to 35° C. with the addition of 3×40 g of Raney nickel. The catalyst is then removed by filtration, the filtrate is concentrated and the residue is taken up in ethyl acetate. After drying over magnesium sulfate and treating with activated carbon and fuller's earth, the filtrate is concentrated and the product is caused to crystallise by the addition of diethyl ether. Yield: 253 g (77% of the theoretical yield over three stages); m.p. 84°–86° C.

Example 1.16: Preparation of 7-methoxycarbonylbenzo-1,2,3-thiadiazole

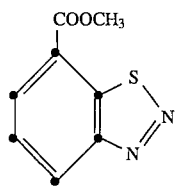

a) 100 g (0.35 mol) of 2-benzylthio-3,5-diaminobenzoic acid methyl ester are added in portions to 250 ml of concentrated hydrochloric acid and 110 ml of water and stirred for 1.5 hours at room temperature. The mixture is then cooled to −5° C. and, over a period of 2.5 hours with stirring, a solution of 48.5 g (0.70 mol) of sodium nitrite in 210 ml of water is added dropwise. The stirring operation is continued for a further 2 hours at 0° C. 190 ml of 50% hypophosphorous acid are then added dropwise over a period of 2½ hours. The temperature is then raised to 20° C. over a period of 19 hours. The resulting product is isolated by filtration, washed with water and dried. For purification, the product is dissolved in ethyl acetate/methylene chloride, filtered through silica gel, evaporated and crystallised by the addition of hexane. Yield: 44.4 g (65% of the theoretical yield); m.p. 132° C.

b) 576 g (2 mol) of 3,5-diamino-2-benzylthiobenzoic acid methyl ester are dissolved in 500 ml of 1,4-dioxane and the batch is added dropwise to 5N hydrochloric acid (3 l) with stirring and cooling to from 0° to 5° C. The fine suspension is then cooled to from −17° to −20° C. and 294 g of sodium nitrite in 500 ml of water are added dropwise below the surface over a period of 1.25 hours. While continuing to stir, the internal temperature is raised to −5° C. over a period of 1 hour and maintained for 2 hours. The suspension is then cooled to −15° C. and introduced in portions, with stirring, into hypophosphorous acid (1.11) cooled to from −10° to −15° C., during which operation nitrogen is evolved. When the addition is complete, the internal temperature is raised to room temperature over a period of 5–6 hours, the precipitate formed is isolated by filtration and stirred with 2.5 l of methylene chloride, and the portion that has not dissolved is again isolated by filtration and the filtrate is separated from the water. The organic phase is then dried over sodium sulfate, stirred with 300 g of silica gel, filtered again and washed with methylene chloride, and the filtrate is concentrated by evaporation. Recrystallisation from methanol gives a total of 244.8 g (63.1% of the theoretical yield) of beige crystals having a melting point of 130°–133° C.

c) 183 g (0.5 mol) of 3,5-diamino-2-n-dodecylthiobenzoic acid methyl ester, dissolved in 200 ml of dioxane, are added dropwise with cooling and stirring at 0°–5° C. to 1.2 l of 5N hydrochloric acid. Stirring is continued for approximately 1 hour to obtain a fine precipitate. The batch is then cooled to from −15° to −21° C. and a solution of 73.5 g of sodium nitrite in 130 ml of water is added dropwise below the surface over a period of 1 hour while continuing to stir at that temperature. The internal temperature is then raised to −5° C. over a period of 1 hour and stirring is continued for a further 3 hours at that temperature. The suspension is then cooled to −10° C. again and is added in portions over a period of 1.5 hours to hypophosphorous acid (280 ml), which is likewise cooled, during which operation nitrogen is evolved. Finally, stirring is continued for 6 hours during which time room temperature is reached, and then the precipitate is isolated by filtration and is worked up as described under 1.16b to form the crude product. For further purification, the latter can also be filtered through a suction filter filled with silica gel and then washed with methylene chloride/hexane (10:1). The batch is concentrated by evaporation and the residue is stirred with 300 ml of methanol to give 46.3 g of beige crystals. A further 7.2 g of crude product can be obtained from the filtrate after crystallisation from ethyl acetate, thus giving a total yield of 53.5 g (55.2% of the theoretical yield), m.p. 130°–133° C.

d) 1.48 g of 1,2,3-benzothiadiazole-7-carboxylic acid are introduced into 40 ml of absolute tetrahydrofuran under a nitrogen atmosphere, and 1.46 g of 1-chloro-N,N-2-trimethylpropenylamine are added dropwise at 0°–3° C. with cooling. The batch is stirred overnight at room temperature, cooled again the day after, and a solution of 1.18 g of pyridine and 0.64 g of absolute methanol is added dropwise thereto. The batch is then stirred for 7 hours at room temperature, diluted with methylene chloride, and ice/water is added. The organic phase is separated off, the aqueous phase is extracted three times with methylene chloride, and the extracts are washed with water, dried and concentrated by evaporation. The crystalline residue is dried at 50° C. under a high vacuum, triturated with a small amount of hexane and filtered and the precipitate is washed thoroughly with hexane to give 1.38 g (87% of the theoretical yield) of pure product having a melting point of 128°–130° C.

e) Using the same method as described in Example 1.16b, 3,5-diamino-2-methylthiobenzoic acid methyl ester is converted into the title compound.

Example 1.17: Preparation of 7-(2-trimethylsilylethoxycarbonyl)-benzo-1,2,3-thiadiazole

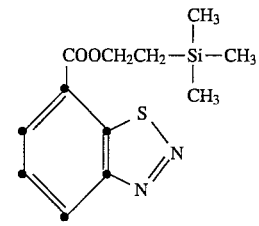

1.99 g (0.01 mol) of 7-benzothiadiazolecarboxylic acid chloride in 18 ml of toluene are added dropwise over a period of 25 minutes to a solution of 1.9 ml (0.013 mol) of 2-trimethylsilylethanol, 2.4 ml (0.017 mol) of triethylamine and 18 ml of toluene. The reaction mixture is then stirred for 16 hours at room temperature and afterwards poured onto ice/water and extracted twice with ethyl acetate. The extracts are combined, washed with water, dried over magnesium sulfate, filtered and concentrated and the same amount of hexane is added and the batch is filtered through silica gel. Concentration gives 2.0 g (71% of the theoretical yield) of product; m.p. 37°–39° C.

Example 1.18: Preparation of 7-(carbonyloxymethyl-O-ethyl-methyl-phosphinic acid ester)-benzo-1,2,3-thiadiazole

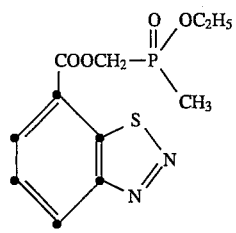

2.6 g (0.013 mol) of benzo-1,2,3-thiadiazole-7-carboxylic acid chloride in 26 ml of dioxane are added dropwise to a solution of 2.2 g of hydroxy-methyl-methyl-phosphinic acid ethyl ester, 3.2 ml (0.023 mol) of triethylamine and 26 ml of dioxane. The reaction mixture is then stirred for 16 hours at room temperature and afterwards filtered through a layer of silica gel and concentrated. The product is recrystallised from ethyl acetate/hexane. Yield: 2.2 g (56 %); m.p. 89°–92° C.

Example 1.19: Preparation of 2-(benzo-1,2,3-thiadiazole-7-carbonyl-1(2'-butyl)-hydrazine

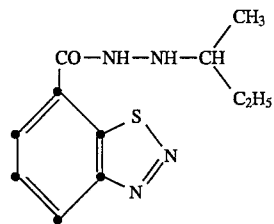

10.5 g of 2-(benzo-1,2,3-thiadiazole-7-carbonyl)-1-(α-methylpropylidene hydrazine are dissolved in 150 ml of dimethylformamide and 100 ml of methylcellosolve and hydrogenated over 7 g of platinum/carbon at room temperature and at normal pressure. The catalyst is then isolated from the solution by filtration and the product remaining after concentrating the filtrate by evaporation is chromatographed on silica gel (ethyl acetate). The product is obtained in the form of white crystals having a melting point of 148°–150° C.

Example 1.20: Preparation of 2-(benzo-1,2,3-thiadiazole-7-carbonyl-1-(2'-butyl)-hydrazine

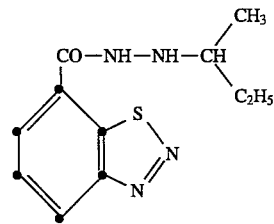

4.8 g of benzo-1,2,3-thiadiazole-7-carboxylic acid hydrazide are dissolved in 300 ml of tetrahydrofuran, and 9.3 g of methyl ethyl ketone and 0.6 g of 5% platinum/carbon catalyst are added. The batch is then hydrogenated at from 20° to 25° C. at normal pressure until the reaction stops, during which time three further additions of catalyst of 2 g each are made. The catalyst is then isolated by filtration, and the filtrate is concentrated by evaporation and recrystallised from ethyl acetate to give white crystals having a melting point of 147°–150° C.

Example 1.21: Preparation of 2-benzylthio-3-nitrobenzoic acid (intermediate)

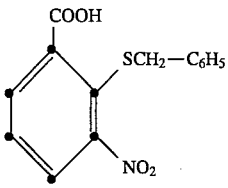

6.85 g (0.055 mol) of benzyl mercaptan are dissolved in 150 ml of dimethylformamide. The batch is then cooled to 0° C. and 15.2 g (0.11 mol) of potassium carbonate are added. 10.6 g (0.050 mol) of 2,3-dinitrobenzoic acid are then added in portions at from 0° to 5° C. and the internal temperature is afterwards raised to room temperature over a period of 24 hours. The reaction mixture is then poured onto ice/water and acidified with hydrochloric acid. The resulting product is filtered, washed with water and dried. Yield: 11.8 g (82% of the theoretical yield); m.p. 152°–153° C.

Example 1.22: Preparation of 3-amino-2-benzylthiobenzoic acid

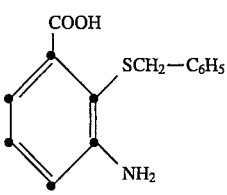

11.0 g (0.038 mol) of 2-benzylthio-3-nitrobenzoic acid are dissolved in ml of tetrahydrofuran and hydrogenated at from 20° to 25° C. in the presence of Raney nickel at normal pressure. The catalyst is then isolated by filtration, the filtrate is concentrated and the resulting product is used directly in the next stage (Example 1.23).

Example 1.23: Preparation of benzo-1,2,3-thiadiazole-7-carboxylic acid

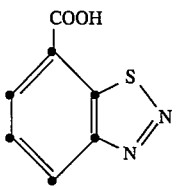

The product obtained in Example 1.22 is reacted analogously to Example 1.7 with hydrochloric acid and sodium nitrite to give the title compound which has a melting point of 260°–262° C.

Example 1.24: Preparation of 3,5-dinitro-2-isopropylthiobenzoic acid methyl ester

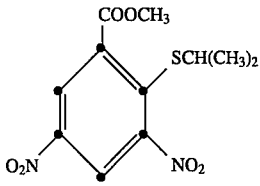

33.2 g (0.240 mol) of potassium carbonate are introduced into 100 ml of dimethylformamide and cooled to –5° C. 37.5 g (0.114 mol) of 2-chloro-3,5-dinitrobenzoic acid (75% with 25% water) in 110 ml of dimethylformamide are then added over a period of 20 minutes, during which time the internal temperature is maintained at from –7° to –3° C. 11.0 ml (0.114 mol) of isopropyl mercaptan (97%) in 20 ml of dimethylformamide are then added dropwise at from −8° to −1° C. over a period of 45 minutes. The batch is then stirred for one hour at 0° C. and the temperature is then raised to 25° C. over a period of 24 hours. 7.5 ml (0.12 mol) of methyl iodide are then added dropwise at room temperature over a period of 30 minutes. The reaction mixture is subsequently stirred for 16 hours at room temperature and then poured onto 500 ml of ice/water, stirred and filtered. The material obtained by filtering with suction is washed with water and dried at room temperature. Yield: 32.6 g (95% of the theoretical yield); m.p. 62°–63° C.

Example 1.25: Preparation of 3,5-diamino-2-isopropylthiobenzoic acid methyl ester

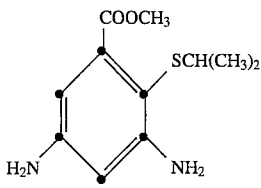

26.6 g (0.0886 mol) of 3,5-dinitro-2-isopropylthiobenzoic acid methyl ester are dissolved in 270 ml of tetrahydrofuran and hydrogenated with the addition of 10 g of Raney nickel at from 30° to 35° C. The catalyst is then isolated by filtration, the filtrate is concentrated and the residue is crystallised from ethyl acetate/hexane. Yield: 20.1 g (94% of the theoretical yield); m.p. 109°–111° C.

Example 1.26: Preparation of 7-methoxycarbonylbenzo-1,2,3-thiadiazole

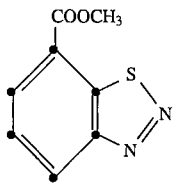

17.0 g (0.0707 mol) of 3,5-diamino-2-isopropylthiobenzoic acid methyl ester are added in portions to 100 ml of concentrated hydrochloric acid and 50 ml of water and the batch is stirred for one hour at room temperature. It is then cooled to −5° C. and a solution of 9.80 g (0.142 mol) of sodium nitrite in 20 ml of water is added dropwise with stirring over a period of 2 hours. Stirring is continued for a further 2 hours at 0° C. and then 23 ml (0.21 mol) of 50% hypophosphorous acid are added dropwise over a period of 30 minutes. The temperature is then raised to 20° C. over a period of 24 hours. 150 ml of water are added to the reaction mixture, and the product is isolated by filtration, washed with water and dried. For purification, the product is taken up in 300 ml of ethyl acetate, boiled under reflux and filtered while hot. Hexane is added to the concentrated filtrate. The resulting product is isolated by filtration and dried. Yield: 7.5 g (55 % of the theoretical yield); m.p. 130°–131° C.

Example 1.27: Preparation of 3,5-dinitro-2-ethylthiobenzoic acid ethyl ester

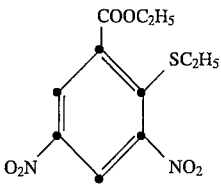

33.2 g (0.240 mol) of potassium carbonate are introduced into 100 ml of dimethylformamide and cooled to −5° C. 37.5 g (0.114 mol) of 2-chloro-3,5-dinitrobenzoic acid (75% with 25% water) dissolved in 120 ml of dimethylformamide are then added over a period of 20 minutes during which time the internal temperature is maintained at from −5° to 0° C. 8.9 ml (0.12 mol) of ethyl mercaptan in 20 ml of dimethylformamide are then added dropwise at −8° C. over a period of 20 minutes. The batch is then stirred for one hour at that same temperature and afterwards the temperature is raised to room temperature over a period of 19 hours. 9.0 ml (0.12 mol) of ethyl bromide in 20 ml of dimethylformamide are then added dropwise over a period of 10 minutes and the reaction mixture is subsequently stirred for 24 hours at room temperature and then poured onto 500 ml of ice/water, stirred and filtered. The material obtained by filtering with suction is washed with water and then dried at room temperature in vacuo and in the presence of phosphorus pentoxide. Yield: 28.7 g (84% of the theoretical yield); m.p. 80°–81° C.

Example 1.28: Preparation of 3,5-diamino-2-ethylthiobenzoic acid ethyl ester

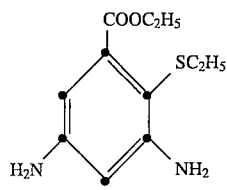

25.9 g (0.0862 mol) of 3,5-dinitro-2-ethylthiobenzoic acid ethyl ester are dissolved in 260 ml of tetrahydrofuran and hydrogenated at 30°–35° C. in the presence of 10 g of Raney nickel. The catalyst is then isolated by filtration, and the residue is taken up in ethyl acetate, dried over magnesium sulfate, filtered and concentrated. Yield: 19.3 g (93% of the theoretical yield).

Example 1.29: Preparation of 5-fluoro-1,2,3-benzothiadiazole-7-carboxylic acid ethyl ester

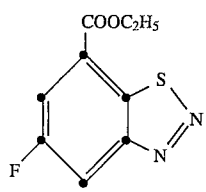

18.7 g (0.078 mol) of 3,5-diamino-2-ethylthiobenzoic acid ethyl ester are introduced into 100 g of anhydrous hydrogen fluoride at from 0° to −12° C. 12.9 g (0.187 mol) of sodium nitrite are then metered in at from 0° to 5° C. over a period of two hours and the reaction mixture is stirred for a further two hours. The diazonium solution is then transferred into a Teflon-coated autoclave and heated to 146° C. therein. After the reaction, the hydrogen fluoride is removed by distillation and the residue is taken up in methylene chloride. After washing with sodium hydrogen carbonate solution and drying with magnesium sulfate, the solution is filtered and concentrated. The resulting crude product is purified over a column of silica gel (solvent: petroleum ether/diethyl ether 2:1). Yield: 1.5 g of yellow crystals having a melting point of 68°–69° C.

Example 1.30: Preparation of 2-benzylthio-3,5-diaminobenzoic acid methyl ester

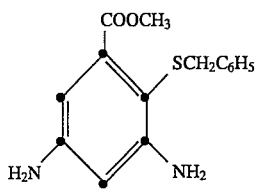

17.7 g of iron turnings are heated to 66° C. in 80 ml of acetic acid (5%) with thorough stirring. A solution of 12.0 g (0.034 mol) of 2-benzylthio-3,5-dinitrobenzoic acid methyl ester in 20 ml of tetrahydrofuran is then slowly added dropwise. After cooling, the batch is neutralised with saturated sodium hydrogen carbonate solution and extracted three times with ethyl acetate. The extracts are washed with water, dried over magnesium sulfate, filtered and concentrated. Crystallisation from diethyl ether gives 8.1E (82% of the theoretical yield) of product; m.p. 80°–82° C.

Example 1.31: Preparation of 3,5-diamino-2-methylthiobenzoic acid methyl ester

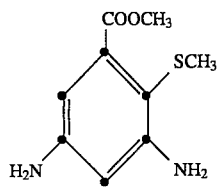

Using the method described in Example 1.30, 3,5-dinitro-2-methylthiobenzoic acid methyl ester is reduced using iron turnings to give the title compound which has a melting point of 102°–104° C.

The following compounds can be prepared in the same manner as described in the Examples above.

In the Tables of Compounds, the associated symbols are used for the following radicals:

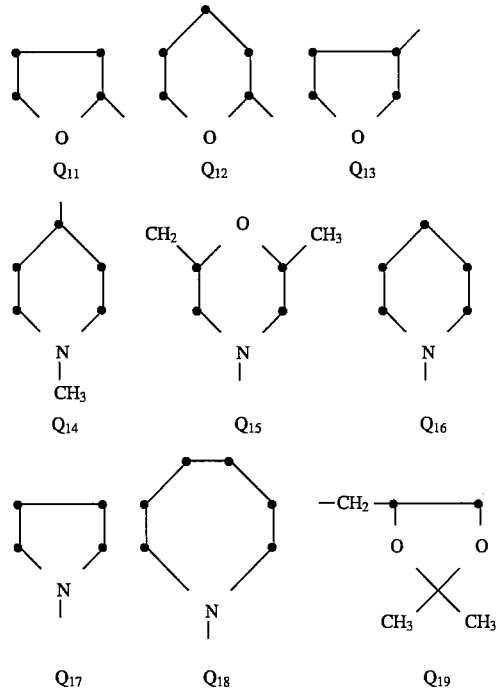

-continued

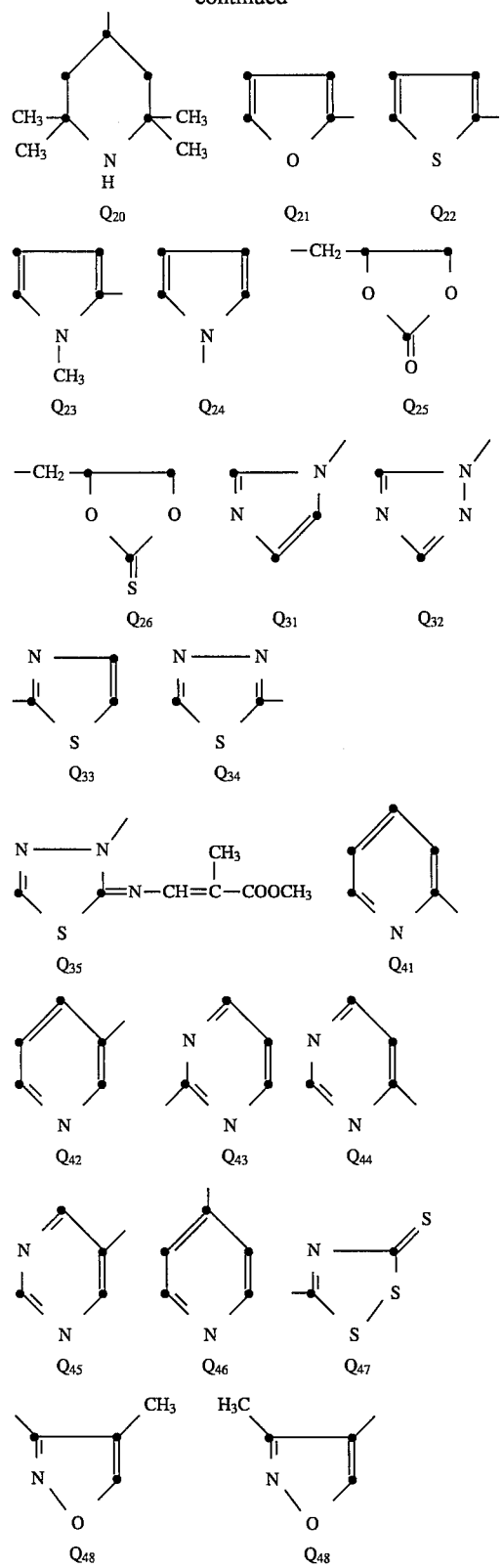

The heterocycles described above may be substituted by low-molecular-weight radicals, such as aliphatic radicals having up to and including carbon atoms, or by halogen atoms or other radicals.

TABLE 1

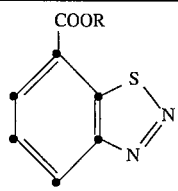

| Comp. no. | R | Physical data |
|---|---|---|
| 1.1 | H | m.p. 262° C. |
| 1.2 | CH$_3$ | m.p. 134–135° C. |
| 1.3 | C$_2$H$_5$ | m.p. 62–63° C. |
| 1.4 | n-C$_3$H$_7$ | m.p. 36–38° C. |
| 1.5 | i-C$_3$H$_7$ | m.p. 78–79° C. |
| 1.6 | n-C$_4$H$_9$ | oil |
| 1.7 | s-C$_4$H$_9$ | |
| 1.8 | t-C$_4$H$_9$ | |
| 1.9 | n-C$_5$H$_{11}$ | m.p. 35–37° C. |
| 1.10 | n-C$_6$H$_{13}$ | |
| 1.11 | n-C$_8$H$_{17}$ | m.p. 41–44° C. |
| 1.12 | 2-Bromoethyl | |
| 1.13 | 2-Chloroethyl | |
| 1.14 | 2-Fluoroethyl | |
| 1.15 | 2-Cyanoethyl | |
| 1.16 | 2-Methoxyethyl | m.p. 30–32° C. |
| 1.17 | 2-n-Butoxyethyl | |
| 1.18 | 2-Allyloxyethyl | |
| 1.19 | 2,2,2-Trichloroethyl | |
| 1.20 | 3-Aethoxypropyl | |
| 1.21 | 3-Acetylpropyl | |
| 1.22 | 3-Chloropropyl(n) | |
| 1.23 | 3-Bromopropyl(n) | |
| 1.24 | 1-Chloroprop-2-yl | |
| 1.25 | 1-Bromoprop-2-yl | |
| 1.26 | 2,3-Dibromopropyl(n) | |
| 1.27 | 2-Nitroethyl | |
| 1.28 | Cyclopropylmethyl | m.p. 46–48° C. |
| 1.29 | 1-Cyclopropyl-eth-1-yl | m.p. 57–60° C. |
| 1.30 | Cyclohexylmethyl | m.p. 62–64° C. |
| 1.31 | Cyclooctylmethyl | |
| 1.32 | 3-Phenylpropyl | b.p. 150° C./0,01 torr |
| 1.33 | 2-Phenylethyl | m.p. 77–79° C. |
| 1.34 | Benzyl | m.p. 94–95° C. |
| 1.35 | 2-Chlorobenzyl | m.p. 126–127° C. |
| 1.36 | 3-Chlorobenzyl | |
| 1.37 | 4-Chlorobenzyl | m.p. 106–108° C. |
| 1.38 | 4-Methylbenzyl | |
| 1.39 | 4-Methoxybenzyl | m.p. 98–100° C. |
| 1.40 | 4-Nitrobenzyl | |
| 1.41 | 2-(4-Methoxyphenyl)ethyl | |
| 1.42 | 2-Phenoxyethyl | m.p. 60–62° C. |
| 1.43 | 2-(4-Chlorophenoxy)ethyl | |
| 1.44 | Allyl | m.p. 57–58° C. |
| 1.45 | 4-Pentenyl | |
| 1.46 | 2-Propynyl | m.p. 129–130° C. |
| 1.47 | 3-Hexynyl | |
| 1.48 | 3-Chloro-but-2-enyl | |
| 1.49 | Cyclopropyl | |
| 1.50 | Cyclopentyl | m.p. 62–64° C. |
| 1.51 | Cyclooctyl | |
| 1.52 | Phenyl | |
| 1.53 | 2-Chlorophenyl | m.p. 108–110° C. |
| 1.54 | 3-Bromophenyl | m.p. 121–123° C. |
| 1.55 | 3,4-Dichlorophenyl | |
| 1.56 | 4-Chloro-2-methyl-phenyl | |
| 1.57 | 4-t-Butylphenyl | m.p. 142–144° C. |
| 1.58 | 3-Nitrophenyl | |

TABLE 1-continued

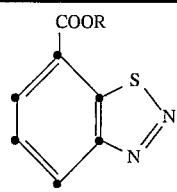

| Comp. no. | R | Physical data |
|---|---|---|
| 1.59 | 4-Nitrophenyl | m.p. 214–216° C. |
| 1.60 | 3-Cyanophenyl | m.p. 181–183° C. |
| 1.61 | 3-Trifluoromethylphenyl | m.p. 107–109° C. |
| 1.62 | 3-N,N-Dimethylaminophenyl | |
| 1.63 | 2-Methoxycarbonyl-phenyl | |
| 1.64 | 3-iodo-prop-2-yn-yl | |
| 1.65 | —CH$_2$—COOCH$_3$ | |
| 1.66 | —CH$_2$—COOC$_2$H$_5$ | |
| 1.67 | —CH(CH$_3$)—COOCH$_3$ | |
| 1.68 | —CH(CH$_3$)—COOC$_2$H$_5$ | m.p. 118–122° C. (S)-enantiomer |
| 1.69 | —CH$_2$CH$_2$N(CH$_3$)$_2$ | |
| 1.70 | 3-N,N-Dimethylaminopropyl | |
| 1.71 | —N═C(CH$_3$)$_2$ | m.p. 127–130° C. |
| 1.72 | —N═⟨pyridyl⟩ | m.p. 125° C. |
| 1.73 | —N═⟨pyridyl⟩—C(CH$_3$)$_3$ | m.p. 112–114° C. |
| 1.74 | —N═C(CH$_3$)CH$_2$OCH$_3$ | |
| 1.75 | —N═C(CN)CONH$_2$ | |
| 1.76 | —N═C(CN)—C$_6$H$_5$ | |
| 1.77 | —N═C(CN)—CONHC$_2$H$_5$ | |
| 1.78 | —N═C(CN)—CONH—CONHC$_2$H$_5$ | |
| 1.79 | —CH$_2$CH$_2$CH$_2$OH | m.p. 26° C. |
| 1.80 | —CH$_2$CH$_2$OH | m.p. 76–79° C. |
| 1.81 | 3-Fluorobenzyl | m.p. 100–102° C. |
| 1.82 | 4-Trifluoromethylbenzyl | |
| 1.83 | CH$_2$CH$_2$Q$_{21}$ | |
| 1.84 | CH$_2$CH$_2$Q$_{41}$ | |
| 1.85 | CH$_2$CH$_2$Q$_{24}$ | |
| 1.86 | Diacetone-D-glucos-3-yl | m.p. 121–123° C. |
| 1.87 | 2-Fluorobenzyl | m.p. 113–115° C. |
| 1.88 | 4-Fluorobenzyl | m.p. 107–109° C. |
| 1.89 | 4-Methylphenyl | m.p. 141–143° C. |
| 1.90 | 2-Methoxycarbonylphenyl | m.p. 120–122° C. |
| 1.91 | 2-Carboxyphenyl | |
| 1.92 | CH$_2$Q$_{11}$ | |
| 1.93 | CH$_2$Q$_{12}$ | |
| 1.94 | CH$_2$Q$_{13}$ | |
| 1.95 | CH$_2$Q$_{14}$ | |
| 1.96 | CH$_2$Q$_{21}$ | m.p. 67° C. |
| 1.97 | CH$_2$Q$_{22}$ | |
| 1.98 | CH$_2$Q$_{23}$ | |
| 1.99 | CH$_2$Q$_{31}$ | |
| 1.100 | CH$_2$Q$_{32}$ | m.p. 166–168° C. |

TABLE 1-continued

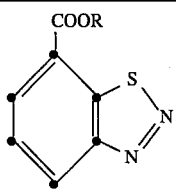

| Comp. no. | R | Physical data |
|---|---|---|
| 1.101 | CH₂Q₄₁ | m.p. 91–93° C. |
| 1.102 | CH₂Q₄₂ | m.p. 97–99° C. |
| 1.103 | CH₂Si(CH₃)₃ | m.p. 59–61° C. |
| 1.104 | CH₂CH₂Si(CH₃)₃ | m.p. 37–39° C. |
| 1.105 | CH₂P(O)(CH₃)OC₂H₅ | m.p. 92° C. |
| 1.106 | CH₂P(O)(OCH₃)₂ | |
| 1.107 | CH₂CH₂P(O)(OC₂H₅)₂ | |
| 1.108 | CH₂CH₂P(O)(OCH₃)₂ | m.p. 86–88° C. |
| 1.109 | CH₂P(O)(CH₃)OCH₃ | |
| 1.110 | CH(CH₃)P(O)(OCH₃)₂ | |
| 1.111 | Si(CH₃)₂C(CH₃)₂CH(CH₃)₂ | |
| 1.112 | Na⊕ | m.p. >250° C. |
| 1.113 | K⊕ | m.p. >250° C. |
| 1.114 | (HN(C₂H₅)₃)⊕ | m.p. 86–89° C. |
| 1.115 | (H₂N(CH₂CH₂OH)₂)⊕ | m.p. 130° C. |
| 1.116 | CH₂-Napth-1-yl | m.p. 123–125° C. |
| 1.117 | CH₂-Naphth-2-yl | |
| 1.118 | CH₂CH₂-Naphth-1-yl | m.p. 94–96° C. |
| 1.119 | 1-Phenethyl | m.p. 50–52° C. |
| 1.120 | 2-Phenyl-prop-2-yl | |
| 1.121 | CH₂CH₂CN | |
| 1.122 | (2-Sulfamoyl)-benzyl | m.p. 198–200° C. |
| 1.123 | CH₂CH₂SCH₃ | |
| 1.124 | 1,2,3,4-Di-O-isopropyliden-D-galacto-pyranos-6-yl | |
| 1.125 | 1,2,5,6-Di-O-isopropyliden-D-mannit-3-yl | |
| 1.126 | 1,2,5,6-Di-O-Isopropyliden-α-D-allo-furanos-3-yl | |
| 1.127 | D-Glucofuranos-3-yl | |
| 1.128 | D-Galactopyranos-6-yl | |
| 1.129 | D-Mannit-3-yl | |
| 1.130 | D-Allofuranos-4-yl | |
| 1.131 | Mannopyranos-1-yl | |
| 1.132 | 2-methyl-D-glucosid-6-yl | |
| 1.133 | 1,2,5,6-Tetraacetyl-D-galactopyranos-3-yl | |
| 1.134 | 2,3,5-Tribenzylribofuranos-1-yl | |
| 1.135 | Cyclohexyl | m.p. 44–46° C. |
| 1.136 | CH₂-Q₄₆ | m.p. 116–118° C. |
| 1.137 | 2,6-Difluorobenzyl | m.p. 117–119° C. |
| 1.138 | CH₂—CCl₂CF₃ | m.p. 71–73° C. |
| 1.139 | 2-Nitrobenzyl | m.p. 196–198° C. |
| 1.140 | 2-Methylbenzyl | m.p. 95–97° C. |
| 1.141 | —CH₂C(OCH₃)₂CH₃ | |
| 1.142 | 3-Methyl-2-nitrobenzyl | m.p. 143–145° C. |
| 1.143 | Cycloheptyl | $n_D^{31}$ = 1,5787 |
| 1.144 | 3-Methoxybenzyl | m.p. 73–75° C. |
| 1.145 | 2,4-Dichlorobenzyl | m.p. 118–120° C. |
| 1.146 | Q₁₉ | m.p. 82–83° C. |
| 1.147 | —CH₂—CH(OH)—CH₂OH | m.p. 75–77° C. |
| 1.148 | —CH₂—CH(OH)—CH₂OCH₃ | |
| 1.149 | —CH₂COC₄H₉(n) | |
| 1.150 | Q₂₀ | m.p. 83–84° C. |
| 1.151 | —CH₂-Q₂₅ | m.p. 113–116° C. |
| 1.152 | —CH₂—CH(OCH₃)—CH₂OCH₃ | |
| 1.153 | —CH₂-Q₂₆ | |

TABLE 1-continued

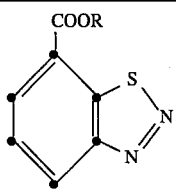

| Comp. no. | R | Physical data |
|---|---|---|
| 1.154 | —CH₂—COC(CH₃)₃ | m.p. 98–100° C. |
| 1.155 | —CH₂—CHOH—CH₂OC₂H₅ | |
| 1.156 | -1/2Mg²⊕ | |
| 1.157 | —CH₂CH₂-Q₁₆ | |
| 1.158 | —CH₂CH₂-Q₁₅ | |
| 1.159 | —CH₂CH₂-Q₄₂ | |
| 1.160 | —CH₂CH₂—N(C₂H₅)₂ | |
| 1.161 | —CH₂CH₂-Q₄₆ | |
| 1.162 | —CH₂CH₂-Q₂₁ | |
| 1.163 | —CH₂CH₂-Q₁₁ | |
| 1.164 | 4'-Trifluormethoxy-benzyl | |
| 1.165 | —CH₂CH₂-Q₂₂ | |
| 1.166 | —CH(CH₃)-Q₄₂ | |
| 1.167 | —CH₂CH₂CH₂—Si(CH₃)₃ | |
| 1.168 | -4-Phenoxy-phenyl | m.p. 97–99° C. |
| 1.169 | -3-Diphenyl | m.p. 108–110° C. |
| 1.170 | —CH(CH₃)-Q₄₁ | |
| 1.171 | -4-Benzyl-benzyl | m.p. 117–119° C. |
| 1.172 | —CH₂—COCH₃ | |
| 1.173 | —CH₂COC₅H₁₁(n) | |
| 1.174 | —CH(CH₃)-Q₂₁ | |
| 1.175 | —C(CH₃)₂-Q₄₆ | |
| 1.176 | 2-(OCF₃)-phenyl | |
| 1.177 | 3-(OCF₂CF₃)-phenyl | |
| 1.178 | 2-Naphthyl | m.p. 136–137° C. |

TABLE 2

COSR

| Comp. no. | R | Physical data |
|---|---|---|
| 2.1 | CH₃ | |
| 2.2 | C₂H₅ | m.p. 87° C. |
| 2.3 | C₃H₇(n) | oil |
| 2.4 | C₄H₉(n) | |
| 2.5 | Benzyl | m.p. 101–104° C. |
| 2.6 | Phenyl | m.p. 137–140° C. |
| 2.7 | 4-Chlorophenyl | m.p. 53–55° C. |
| 2.8 | CH₂COOCH₃ | m.p. 126–129° C. |
| 2.9 | CH₂COOC₂H₅ | |
| 2.10 | 4-Methylphenyl | |
| 2.11 | n-Hexyl | |
| 2.12 | Cyclohexyl | |
| 2.13 | Cyclopentyl | |
| 2.14 | H | |
| 2.15 | Na⊕ | |
| 2.16 | K⊕ | |

TABLE 3

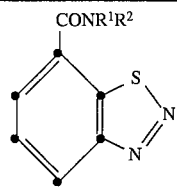

| Comp. no. | NR$^1$R$^2$ | Physical data |
|---|---|---|
| 3.1 | NH$_2$ | m.p. >270° C. |
| 3.2 | NHCH$_3$ | m.p. 243–247° C. |
| 3.3 | Piperidinyl | m.p. 91,5–93,5° C. |
| 3.4 | Morpholinyl | m.p. 138–141° C. |
| 3.5 | NHCH(CH$_3$)C$_2$H$_5$ | m.p. 134° C. |
| 3.6 | NH—C$_6$H$_5$ | m.p. 180–183° C. |
| 3.7 | NH—CH$_2$COOC$_2$H$_5$ | m.p. 119–122° C. |
| 3.8 | N(CH$_3$)$_2$ | m.p. 83–85° C. |
| 3.9 | NH—CH$_2$COOH | m.p. 207° C. |
| 3.10 | Pyrrolidinyl | |
| 3.11 | Q$_{15}$ | m.p. 150–153° C. |
| 3.12 | Q$_{47}$ | |
| 3.13 | N(CH$_2$CN)$_2$ | m.p. 197–199° C. |
| 3.14 | N(CH$_2$CH$_2$CN)$_2$ | |
| 3.15 | NHCH$_2$CH$_2$OCH$_3$ | |
| 3.16 | Q$_{24}$ | |
| 3.17 | Q$_{31}$ | m.p. 119–121° C. |
| 3.18 | Q$_{32}$ | |
| 3.19 | NH-Q$_{33}$ | m.p. 225–227° C. |
| 3.20 | NH-Q$_{34}$ | decomp. 303° C. |
| 3.21 | NH-Q$_{41}$ | |
| 3.22 | NH-Q$_{43}$ | |
| 3.23 | NH-Q$_{44}$ | |
| 3.24 | NHCH$_2$C≡CH | m.p. 229–231° C. |
| 3.25 | NH—CH(CH$_3$)COOCH$_3$ | |
| 3.26 | N(CH$_2$CH=CH$_2$)$_2$ | m.p. 119° C. |
| 3.27 | NH(5-Ethyl-6-chloro-pyrimidin-4-yl) | m.p. 185–187° C. |
| 3.28 | ![structure] -N(Q$_{34}$)(C(COOCH$_3$)=C(CH$_3$)) | m.p. 140–142° C. |
| 3.29 | ![structure] -N(Q$_{34}$)(C(COOCH$_3$)=C(C$_2$H$_5$)) | m.p. 142–145° C. |
| 3.30 | ![structure with N-N=N, S, COOCH$_3$, CH$_3$] | m.p. 203–206° C. |
| 3.31 | N(CH$_3$)OCH$_3$ | m.p. 115–117° C. |
| 3.32 | N(CH$_3$)OCH(CH$_3$)$_2$ | |
| 3.33 | N(C$_2$H$_5$)OCH$_3$ | |
| 3.34 | N(i-C$_4$H$_9$)OCH$_3$ | |
| 3.35 | NHCH$_2$CN | |
| 3.36 | NH-Benzyl | m.p. 148–150° C. |
| 3.37 | NH-4-Chlorobenzyl | |
| 3.38 | NH-3-Chlorobenzyl | |

TABLE 3-continued

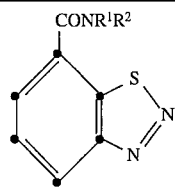

| Comp. no. | NR$^1$R$^2$ | Physical data |
|---|---|---|
| 3.39 | NH-2-Chlroboenzyl | m.p. 173–175° C. |
| 3.40 | NH-2,4-Dichlorobenzyl | m.p. 171–174° C. |
| 3.41 | NH-3,4-Dichlorobenzyl | m.p. 185–188° C. |
| 3.42 | NH-2-FLuorobenzyl | m.p. 145–147° C. |
| 3.43 | NH-4-Fluorobenzyl | |
| 3.44 | NH-2-Methylbenzyl | m.p. 164–165° C. |
| 3.45 | NH—CH(Methyl)-Q$_{21}$ | m.p. 127–129° C. |
| 3.46 | 2-Methylpiperidine-1-yl | m.p. 94–96° C. |
| 3.47 | NH-4-Methylbenzyl | |
| 3.48 | N(Methyl)-benzyl | m.p. 101–103° C. |
| 3.49 | NH—CH$_2$-Q$_{21}$ | m.p. 141–143° C. |
| 3.50 | NH-Q$_{48}$ | m.p. 278–281° C. |
| 3.51 | NHOH | decomp. >87° C. |
| 3.52 | Q$_{18}$ | |

TABLE 4

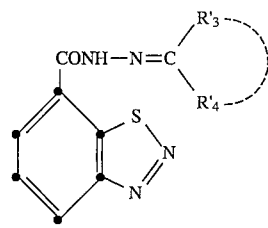

| Comp. | R$_3$' | R$_4$' | Physical data |
|---|---|---|---|
| 4.1 | CH$_3$ | CH$_3$ | m.p. 166–168° C. |
| 4.2 | CH$_3$ | C$_2$H$_5$ | m.p. 159–162° C. |
| 4.3 | C$_2$H$_5$ | C$_2$H$_5$ | |
| 4.4 | C$_3$H$_7$-n | C$_3$H$_7$-n | |
| 4.5 | C$_4$H$_9$-n | C$_4$H$_9$-n | |
| 4.6 | C$_4$H$_9$-s | C$_4$H$_9$-s | |
| 4.7 | C$_6$H$_{13}$-n | C$_6$H$_{13}$-n | |
| 4.8 | —CH$_2$CH$_2$CH$_2$— | | |
| 4.9 | —CH$_2$CH$_2$CH$_2$CH$_2$— | | m.p. 154–157° C. |
| 4.10 | —CH$_2$—CH$_2$—CH$_2$—CH$_2$—CH$_2$— | | |
| 4.11 | —CH$_2$CH$_2$CH$_2$CH$_2$CH$_2$—CH$_2$— | | m.p. 134–136° C. |
| 4.12 | H | CH$_3$ | |
| 4.13 | H | C$_2$H$_5$ | |
| 4.14 | H | CH=CH$_2$ | |
| 4.15 | H | C$_6$H$_5$ | m.p. 266–268° C. |
| 4.16 | H | C$_6$H$_4$Cl(2) | |
| 4.17 | H | C$_6$H$_4$Cl(4) | |
| 4.18 | CH$_3$ | C$_6$H$_5$ | |
| 4.19 | CH$_3$ | C$_6$H$_3$Cl$_2$(2,4) | m.p. 209–210° C. |
| 4.20 | H | Q$_{41}$ | m.p. 226–228° C. |
| 4.21 | H | Q$_{42}$ | |
| 4.22 | CH$_3$ | Q$_{41}$ | |
| 4.23 | H | Q$_{21}$ | m.p. 231–232° C. |
| 4.24 | H | CCl$_3$ | m.p. 174–175° C. |
| 4.25 | CH$_3$ | CH$_2$OCH$_3$ | |

TABLE 5

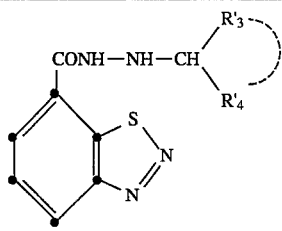

| Comp. no. | $R_3'$ | $R_4'$ | Physical data |
|---|---|---|---|
| 5.1 | $CH_3$ | $CH_3$ | m.p. 145–147° C. |
| 5.2 | $CH_3$ | $C_2H_5$ | m.p. 148–150° C. |
| 5.3 | $C_2H_5$ | $C_2H_5$ | m.p. 148–150° C. |
| 5.4 | $C_3H_7$-n | $C_3H_7$-n | |
| 5.5 | $C_4H_9$-n | $C_4H_9$-n | |
| 5.6 | $C_6H_{13}$-n | $C_6H_{13}$-n | |
| 5.7 | | $CH_2(CH_2)_2CH_2$ | |
| 5.8 | | $CH_2(CH_2)_3CH_2$ | m.p. 154–156° C. |
| 5.9 | | $CH_2(CH_2)_4CH_2$ | m.p. 166–168° C. |
| 5.10 | H | $CH_3$ | |
| 5.11 | H | $C_2H_5$ | |
| 5.12 | H | $C_6H_5$ | m.p. >166° C. |

TABLE 5-continued

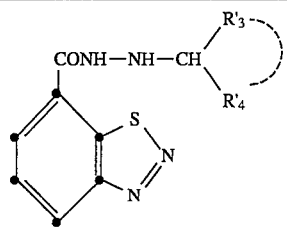

| Comp. no. | $R_3'$ | $R_4'$ | Physical data |
|---|---|---|---|
| 5.13 | H | o-Cl—$C_6H_4$ | |
| 5.14 | $CH_3$ | $C_6H_5$ | |
| 5.15 | $CH_3$ | 2,4-Di-Cl—$C_6H_3$ | |
| 5.16 | H | $Q_{41}$ | |
| 5.17 | H | $Q_{42}$ | |
| 5.18 | $CH_3$ | $Q_{41}$ | |
| 5.19 | H | $Q_{21}$ | |
| 5.20 | $CH_3$ | $CH_2OCH_3$ | |
| 5.21 | $CH_3$ | $CH_2CH_2OCH_3$ | |
| 5.22 | H | $Q_{24}$ | |

TABLE 6

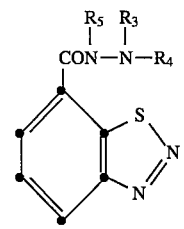

| Comp. no. | $R_5$ | $R_4$ | $R_3$ | Physical data |
|---|---|---|---|---|
| 6.1 | H | H | H | m.p. 270–272° C. |
| 6.2 | H | $CH_3$ | H | |
| 6.3 | H | $COCH_3$ | H | |
| 6.4 | H | $COC_2H_5$ | H | |
| 6.5 | H | $COCH=CH_2$ | H | |
| 6.6 | H | $COC(Cl)=C(Cl)_2$ | H | |
| 6.7 | $COCH_3$ | $COCH_3$ | H | |
| 6.8 | H | H | $C_6H_5$ | |
| 6.9 | H | H | $Q_{41}$ | |
| 6.10 | H | $COCH_3$ | $Q_{21}$ | |
| 6.11 | H | H | $Q_{34}$ | |
| 6.12 | $CH_3$ | $COCH_3$ | $Q_{41}$ | |
| 6.13 | H | $COCH_3$ | $Q_{41}$ | |
| 6.14 | H | $COCH_2OCH_3$ | H | |
| 6.15 | H | $COCH_2OCH_3$ | $Q_{41}$ | |
| 6.16 | H | $COC(Cl)=C(Cl)_2$ | $Q_{41}$ | |
| 6.17 | $COCH_3$ | $COCH_3$ | $Q_{41}$ | |
| 6.18 | H | H | $Q_{43}$ | |
| 6.19 | H | $COCH_3$ | $Q_{44}$ | |
| 6.20 | H | $COCH_3$ | $Q_{43}$ | |
| 6.21 | H | H | $Q_{44}$ | |
| 6.22 | H | H | $Q_{21}$ | |
| 6.23 | H | sec-Butyl | sec-Butyl | m.p. 92–95° C. |
| 6.24 | H | $COCH_3$ | sec-Butyl | m.p. 100–102° C. |

TABLE 6-continued

[Structure: benzothiadiazole with CON(R5)-N(R3)(R4) substituent]

| Comp. no. | R5 | R4 | R3 | Physical data |
|---|---|---|---|---|
| 6.25 | H | CH$_3$ | CH$_3$ | |
| 6.26 | H | CH(CH$_3$)CH$_2$OCH$_3$ | CH(CH$_3$)CH$_2$OCH$_3$ | |
| 6.27 | H | C$_2$H$_5$ | C$_2$H$_5$ | |
| 6.28 | CH$_3$ | sec-Butyl | sec-Butyl | |
| 6.29 | H | COCH$_3$ | CH$_3$ | |
| 6.30 | H | COCH$_3$ | CH$_2$OCH$_3$ | |
| 6.31 | H | COCH$_3$ | C$_2$H$_5$ | |
| 6.32 | H | COC$_2$H$_5$ | sec-Butyl | |
| 6.33 | H | COCH$_2$OCH$_3$ | sec-Butyl | |
| 6.34 | H | COCH$_2$OCH$_3$ | C$_2$H$_5$ | |
| 6.35 | H | COCH$_3$ | n-Propyl | |
| 6.36 | H | COCH$_3$ | i-Propyl | |
| 6.37 | H | n-Propyl | n-Propyl | |
| 6.38 | H | i-Propyl | i-Propyl | m.p. 173–175° C. |

TABLE 7

[Structure: benzothiadiazole with X, Y, Z substituents]

| Comp. no. | Y | X | Z | Physical data |
|---|---|---|---|---|
| 7.1 | Br | H | COOCH$_3$ | m.p. 138–141° C. |
| 7.2 | Cl | H | COOCH$_3$ | m.p. 142° C. |
| 7.3 | Cl | H | COOH | |
| 7.4 | H | 6-Cl | COOCH$_3$ | m.p. 111–114° C. |
| 7.5 | H | 6-Cl | COOH | m.p. 255–260° C. |
| 7.6 | H | 6-F | COOCH$_3$ | m.p. 122–125° C. |
| 7.7 | Br | H | COOH | |
| 7.8 | H | 6-F | COOH | |
| 7.9 | H | 6-F | COOC$_2$H$_5$ | |
| 7.10 | H | 6-F | COOC$_3$H$_7$(n) | |
| 7.11 | H | 6-F | COOCH(CH$_3$)COOC$_2$H$_5$ | |
| 7.12 | Cl | H | CN | |
| 7.13 | H | 4-Br | CN | |
| 7.14 | H | 4-Cl | CN | |
| 7.15 | H | 6-F | CN | |
| 7.16 | F | H | CN | |
| 7.17 | H | 4-F | CN | |
| 7.18 | H | 4-COOH | COOH | |
| 7.19 | H | 4-COOCH$_3$ | COOCH$_3$ | |
| 7.20 | H | 6-OH | COOH | |
| 7.21 | H | 6-OH | COOCH$_3$ | |
| 7.22 | H | 6-OCH$_3$ | COOCH$_3$ | |
| 7.23 | H | 4-CH$_3$ | COOCH$_3$ | |
| 7.24 | F | 4-F | COOCH$_3$ | |
| 7.25 | F | 6-F | COOCH$_3$ | |
| 7.26 | H | H | CN | m.p. 116–118° C. |
| 7.27 | SO$_3$H | H | CN | |
| 7.28 | SO$_2$H | H | COOH | |
| 7.29 | SO$_3$H | H | COOCH$_3$ | |
| 7.30 | NO$_2$ | H | COOH | |
| 7.31 | NO$_2$ | H | COOCH$_3$ | |
| 7.32 | SO$_3$Na | H | COONa | |
| 7.33 | SO$_3$Na | H | CN | |
| 7.34 | NH$_2$ | H | CN | |

TABLE 7-continued

| Comp. no. | Y | X | Z | Physical data |
|---|---|---|---|---|
| 7.35 | NH$_2$ | H | COOH | |
| 7.36 | NH$_2$ | H | COOCH$_3$ | |
| 7.37 | SO$_3$H | 6-F | COOCH$_3$ | |
| 7.38 | H | 6-F | CONHOH | |
| 7.39 | H | 6-F | CONHNH$_2$ | |
| 7.40 | H | 6-Cl | CONHNH$_2$ | decomp. 240° C. |
| 7.41 | H | 6-Cl | CONHNH—C(CH$_3$)(C$_2$H$_5$) | |
| 7.42 | H | 6-F | COOCH$_2$-Q$_{21}$ | |
| 7.43 | H | 6-Cl | CONHQ$_{34}$ | |
| 7.44 | H | 6-COOH | COOH | |
| 7.45 | H | 6-Cl | CONH—N=C(CH$_3$)(C$_2$H$_5$) | |
| 7.46 | H | 6-Cl | COO—N=(cyclohexylidene) | |
| 7.47 | F | H | COO—N=C(CN)(CONH$_2$) | |
| 7.48 | F | H | COOQ$_{46}$ | |
| 7.49 | H | 6-Cl | COOCH$_2$-Q$_{32}$ | |
| 7.50 | NO$_2$ | H | COQ$_{16}$ | |
| 7.51 | H | 6-Cl | CN | |
| 7.52 | F | H | COO-benzyl | |
| 7.53 | H | 6-F | COO-benzyl | |
| 7.54 | H | 4-F | COO-benzyl | |
| 7.55 | NH$_2$ | H | COO-benzyl | |
| 7.56 | NO$_2$ | H | COO-benzyl | |
| 7.57 | OH | H | COO—CH$_3$ | |
| 7.58 | F | H | CONH$_2$ | |
| 7.59 | F | H | COOH | |
| 7.60 | F | H | COOCH$_3$ | |
| 7.61 | F | H | COOC$_2$H$_5$ | m.p. 68–69° C. |
| 7.62 | F | H | COOCH$_2$CH$_2$CH$_3$ | |
| 7.63 | F | H | COOCH(CH$_3$)$_2$ | |
| 7.64 | F | H | COOCH$_2$C$_6$H$_4$-o-Cl | |
| 7.65 | F | H | COOCH$_2$CH$_2$Si(CH$_3$)$_3$ | |
| 7.66 | F | H | CON(OCH$_3$)CH$_3$ | |

TABLE 8

[Structure: benzothiadiazole with X*, Y*, Z* substituents]

| Comp. no. | Y* | X* | Z* | Physical data |
|---|---|---|---|---|
| 8.1 | H | H | COCl | m.p. 107° C. |
| 8.2 | H | H | COBr | |
| 8.3 | H | H | COF | |
| 8.4 | H | H | COJ | |
| 8.5 | H | H | CO—OCOCH₃ | |
| 8.6 | H | H | COO—CO—[benzothiadiazolyl] | m.p. 117–119° C. |
| 8.7 | H | H | COOCO-Phenyl | |
| 8.8 | F | 6-F | COCl | |
| 8.9 | H | 6-F | COCl | |
| 8.10 | F | H | COCl | |
| 8.11 | H | 6-F | COO—CO—[benzothiadiazolyl] | |
| 8.12 | F | H | COO—CO—[benzothiadiazolyl] | |
| 8.13 | H | H | COOSO₂—CH₃ | |
| 8.14 | H | H | COOOCO₂-Phenyl | |

In Table 9 below intermediate compounds are exemplified which constitute part of this invention.

TABLE 9

[Structure: benzene ring with X, Y, Z, SE, NH₂ substituents]

| Comp. no. | X | Y | Z | E | Physical data |
|---|---|---|---|---|---|
| 9.1 | H | NH₂ | COOH | CH₂C₆H₅ | m.p. 124–125° C. |
| 9.2 | H | NH₂ | COOCH₃ | CH₂C₆H₅ | m.p. 84–86° C. |
| 9.3 | H | NH₂ | COOC₂H₅ | CH₂C₆H₅ | |
| 9.4 | H | NH₂ | COOCH(CH₃)₂ | CH₂C₆H₅ | |
| 9.5 | H | NH₂ | COOCH₂CH₂CH₃ | CH₂C₆H₅ | |
| 9.6 | H | NH₂ | COO(CH₂)₃CH₃ | CH₂C₆H₅ | |
| 9.7 | H | NH₂ | COOCH₂C₆H₅ | CH₂C₆H₅ | |
| 9.8 | H | H | COOH | CH₂C₆H₅ | m.p. 98° C. |
| 9.9 | H | H | COOCH₃ | CH₂C₆H₆ | |
| 9.10 | H | H | COOC₂H₅ | CH₂C₆H₅ | |
| 9.11 | H | H | COOCH(CH₃)₂ | CH₂C₆H₅ | |
| 9.12 | H | H | COOCH₂CH₂CH₃ | CH₂C₆H₅ | |
| 9.13 | H | H | COO(CH₂)₃CH₃ | CH₂C₆H₅ | |
| 9.14 | H | H | COOCH₂C₆H₅ | CH₂C₆H₅ | |
| 9.15 | H | NH₂ | COOH | CH(CH₃)₂ | |
| 9.16 | H | NH₂ | COOCH₃ | CH(CH₃)₂ | m.p. 109–110° C. |
| 9.17 | H | NH₂ | COOC₂H₅ | CH(CH₃)₂ | |
| 9.18 | H | NH₂ | COOCH(CH₃)₂ | CH(CH₃)₂ | |
| 9.19 | H | NH₂ | COOCH₂CH₂CH₃ | CH(CH₃)₂ | |
| 9.20 | H | NH₂ | COO(CH₂)₃CH₃ | CH(CH₃)₂ | |

TABLE 9-continued

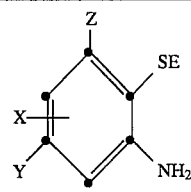

| Comp. no. | X | Y | Z | E | Physical data |
|---|---|---|---|---|---|
| 9.21 | H | $NH_2$ | $COOCH_2C_6H_5$ | $CH(CH_3)_2$ | |
| 9.22 | H | $NH_2$ | COOH | H | |
| 9.23 | H | $NH_2$ | $COOCH_3$ | H | |
| 9.24 | H | $NH_2$ | $COOC_2H_5$ | H | |
| 9.25 | H | $NH_2$ | $COOCH(CH_3)_2$ | H | |
| 9.26 | H | $NH_2$ | $COOCH_2CH_2CH_3$ | H | |
| 9.27 | H | $NH_2$ | $COOCH_2C_6H_5$ | H | |
| 9.28 | H | H | COOH | $CH(CH_3)_2$ | |
| 9.29 | H | H | $COOCH_3$ | $CH(CH_3)_2$ | |
| 9.30 | H | H | $COOC_2H_5$ | $CH(CH_3)_2$ | |
| 9.31 | H | H | $COOCH(CH_3)_2$ | $CH(CH_3)_2$ | |
| 9.32 | H | H | $COOCH_2CH_2CH_3$ | $CH(CH_3)_2$ | |
| 9.33 | H | H | $COOCH_2C_6H_5$ | $CH(CH_3)_2$ | |
| 9.34 | H | Br | COOH | $CH_2C_6H_5$ | |
| 9.35 | H | Br | $COOCH_3$ | $CH_2C_6H_5$ | |
| 9.36 | H | Br | $COOC_2H_5$ | $CH_2C_6H_5$ | |
| 9.37 | H | Br | $COOCH(CH_3)_2$ | $CH_2C_6H_5$ | |
| 9.38 | H | Br | $COOCH_2CH_2CH_3$ | $CH_2C_6H_5$ | |
| 9.39 | H | Br | $COOCH_2C_6H_5$ | $CH_2C_6H_5$ | |
| 9.40 | H | Cl | COOH | $CH_2C_6H_5$ | |
| 9.41 | H | Cl | $COOCH_3$ | $CH_2C_6H_5$ | |
| 9.42 | H | Cl | $COOC_2H_5$ | $CH_2C_6H_5$ | |
| 9.43 | H | Cl | $COOCH(CH_3)_2$ | $CH_2C_6H_5$ | |
| 9.44 | H | Cl | $COOCH_2CH_2CH_3$ | $CH_2C_6H_5$ | |
| 9.45 | H | Cl | $COOCH_2C_6H_5$ | $CH_2C_6H_5$ | |
| 9.46 | Cl | H | $COOCH_3$ | $CH_2C_6H_5$ | |
| 9.47 | Cl | H | COOH | $CH_2C_6H_5$ | |
| 9.48 | F | H | COOH | $CH_2C_6H_5$ | |
| 9.49 | F | H | $COOCH_3$ | $CH_2C_6H_5$ | |
| 9.50 | F | H | $COOC_2H_5$ | $CH_2C_6H_5$ | |
| 9.51 | F | H | $COOCH(CH_3)_2$ | $CH_2C_6H_5$ | |
| 9.52 | F | H | $COOCH_2CH_2CH_3$ | $CH_2C_6H_5$ | |
| 9.53 | F | H | $COOCH_2C_6H_5$ | $CH_2C_6H_5$ | |
| 9.54 | F | H | $COOCH_3$ | $CH(CH_3)_2$ | |
| 9.55 | F | H | $COOC_2H_5$ | $C_2H_5$ | |
| 9.56 | F | H | $COOCH_3$ | $CH_3$ | |
| 9.57 | H | $NH_2$ | COOH | $CH_3$ | |
| 9.58 | H | $NH_2$ | $COOCH_3$ | $CH_3$ | m.p. 102–104° C. |
| 9.59 | H | $NH_2$ | $COOC_2H_5$ | $CH_3$ | |
| 9.60 | H | $NH_2$ | $COOCH(CH_3)_2$ | $CH_3$ | |
| 9.61 | H | $NH_2$ | $COOCH_2CH_2CH_3$ | $CH_3$ | |
| 9.62 | H | $NH_2$ | $COOCHC_6H_5$ | $CH_3$ | |
| 9.63 | H | $NH_2$ | COOH | $C_2H_5$ | |
| 9.64 | H | $NH_2$ | $COOCH_3$ | $C_2H_5$ | |
| 9.65 | H | $NH_2$ | $COOC_2H_5$ | $C_2H_5$ | oil |
| 9.66 | H | $NH_2$ | $COOCH(CH_3)_2$ | $C_2H_5$ | |
| 9.67 | H | $NH_2$ | $COOCH_2CH_2CH_3$ | $C_2H_5$ | |
| 9.68 | H | $NH_2$ | $COOCH_2C_6H_5$ | $C_2H_5$ | |

9.69  H  $NH_2$  $COOCH_3$

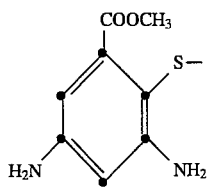

9.70  H  $NH_2$  $COOCH_2C_6H_5$

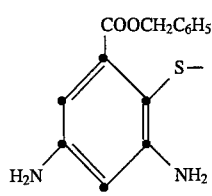

TABLE 9-continued

```
        Z
         \
    X     SE
     \   /
      \ /
      / \
     /   \
    Y     NH2
```

| Comp. no. | X | Y | Z | E | Physical data |
|---|---|---|---|---|---|
| 9.71 | H | NH$_2$ | COO(CH$_2$)$_2$CH$_3$ | (structure below) | |

```
   COO(CH2)2CH3
        |
        S—
       /
   H2N   NH2
```

| Comp. no. | X | Y | Z | E | Physical data |
|---|---|---|---|---|---|
| 9.72 | H | NH$_2$ | COOCH$_3$ | CH$_3$(CH$_2$)$_{11}$ | |
| 9.73 | H | NH$_2$ | COOCH$_2$C$_6$H$_5$ | CH$_3$(CH$_2$)$_{11}$ | |

2. Formulation Examples for liquid active ingredients of formula I (throughout, percentages are by weight)

| 2.1. Emulsifiable concentrates | a) | b) | c) |
|---|---|---|---|
| compound of Tables 1 to 8 | 25% | 40% | 50% |
| calcium dodecylbenzenesulfonate | 5% | 8% | 6% |
| castor oil polyethylene glycol ether (36 moles of ethylene oxide) | 5% | — | — |
| tributylphenol polyethylene glycol ether (30 moles of ethylene oxide) | — | 12% | 4% |
| cyclohexanone | — | 15% | 20% |
| xylene mixture | 65% | 25% | 20% |

Emulsions of any desired concentration can be produced from such concentrates by dilution with water.

| 2.2. Solutions | a) | b) | c) | d) |
|---|---|---|---|---|
| compound of Tables 1 to 8 | 80% | 10% | 5% | 95% |
| ethylene glycol monomethyl ether | 20% | — | — | — |
| polyethylene glycol (mol. wt. 400) | — | 70% | — | — |
| N-methyl-2-pyrrolidone | — | 20% | — | — |
| epoxidised coconut oil | — | — | 1% | 5% |
| petroleum fraction (boiling range 160–190° C.) | — | — | 94% | — |

These solutions are suitable for application in the form of micro-drops.

| 2.3. Granulates | a) | b) |
|---|---|---|
| compound of Tables 1 to 8 | 5% | 10% |
| kaolin | 94% | — |
| highly dispersed silicic acid | 1% | — |
| attapulgite | — | 90% |

The active ingredient is dissolved in methylene chloride, the solution is sprayed onto the carrier, and the solvent is subsequently evaporated off in vacuo.

| 2.4. Dusts | a) | b) |
|---|---|---|
| compound of Tables 1 to 8 | 2% | 5% |
| highly dispersed silicic acid | 1% | 5% |
| talcum | 97% | — |
| kaolin | — | 90% |

Ready-for-use dusts are obtained by intimately mixing the carriers with the active ingredient.

Formulation Examples for solid active ingredients of formula I (throughout, percentages are by weight):

| 2.5. Wettable powders | a) | b) | c) |
|---|---|---|---|
| compound of Tables 1 to 8 | 25% | 50% | 75% |
| sodium lignosulfonate | 5% | 5% | — |
| sodium lauryl sulfate | 3% | — | 5% |
| sodium diisobutylnaphthalene-sulfonate | — | 6% | 10% |
| octylphenol polyethylene glycol ether (7–8 moles of ethylene oxide) | — | 2% | — |
| highly dispersed silicic acid | 5% | 10% | 10% |
| kaolin | 62% | 27% | — |

The active ingredient is thoroughly mixed with the adjuvants and the mixture is ground homogeneously in a suitable mill, affording wettable powders which can be diluted with water to give suspensions of the desired concentration.

| 2.6. Emulsifiable concentrate | |
|---|---|
| compound of Tables 1 to 8 | 10% |
| octylphenol polyethylene glycol ether (4–5 moles of ethylene oxide) | 3% |
| calcium dodecylbenzenesulfonate | 3% |
| castor oil polyglycol ether (35 moles of ethylene oxide) | 4% |
| cyclohexanone | 30% |
| xylene mixture | 50% |

Emulsions of any required concentration can be obtained from this concentrate by dilution with water.

| 2.7. Dusts | a) | b) |
|---|---|---|
| compound of Tables 1 to 8 | 5% | 8% |
| talcum | 95% | — |
| kaolin | — | 92% |

Ready-for-use dusts are obtained by mixing the active ingredient with the carriers and grinding the mixture in a suitable mill.

| 2.8. Extruder granulate | |
|---|---|
| compound of Tables 1 to 8 | 10% |
| sodium lignosulfonate | 2% |
| carboxymethylcellulose | 1% |
| kaolin | 87% |

The active ingredient is mixed and ground with the adjuvants, and the mixture is subsequently moistened with water. The mixture is extruded and then dried in a stream of air.

| 2.9. Coated granulate | |
|---|---|
| compound of Tables 1 to 8 | 3% |
| polyethylene glycol (mol. wt. 200) | |
| kaolin | 94% |

The finely ground active ingredient is uniformly applied, in a mixer, to the kaolin moistened with polyethylene glycol. Non-dusty coated granulates are obtained in this manner.

| 2.10. Suspension concentrate | |
|---|---|
| compound of Tables 1 to 8 | 40% |
| ethylene glycol | 10% |
| nonylphenol polyethylene glycol ether (15 moles of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the adjuvants, giving a suspension concentrate from which suspensions of any desired concentration can be obtained by dilution with water.

3. Biological Examples

Example 3.1: Immunising action against *Colletotrichum lagenarium* on *Cucumis sativus* L.

A) Foliar application

After a cultivation period of 2 weeks, cucumber plants are sprayed with a spray mixture (concentration: 0.02 % active ingredient) prepared from a wettable powder formulation of the test compound.

After one week the plants are infected with a spore suspension ($1.5 \times 10^5$ spores/ml) of the fungus and incubated in the dark for 36 hours at high humidity and at a temperature of 23° C. Incubation is then continued at normal humidity and 22° to 23° C.

Evaluation of the protective action is made 7 to 8 days after infection and is based on the fungus attack.

B) Soil application

After a cultivation period of 2 weeks, cucumber plants are treated by soil application with a spray mixture (concentration: 0.002 % active ingredient, based on the volume of the soil) prepared from a wettable powder formulation of the test compound.

One week later the plants are infected with a spore suspension ($1.5 \times 10^5$ spores/ml) of the fungus and incubated in the dark for 36 hours at high humidity and at a temperature of 23° C. Incubation is then continued at normal humidity and 22°–23° C.

Evaluation of the protective action is made 7 to 8 days after infection and is based on the fungus attack.

C) Dressing

Cucumber seeds are dressed with a solution of the test compound (concentration: 180 g of active ingredient/100 kg of seed). The seeds are sown. After 4 weeks the plants are infected with a spore suspension ($1.5 \times 10^5$ spores/ml) of the fungus and incubated for 36 hours at high humidity and at a temperature of 23° C. Incubation is then continued at normal humidity and 22° to 23° C. Evaluation of the protective action is made 7 to 8 days after infection and is based on the fungus attack.

Untreated and infected control plants in tests A and B and infected plants the seeds of which have not been treated in test C exhibit 100% fungus attack.

Compounds of Tables 1 to 7 result in good immunisation against *Colletotrichum lagenarium*. Thus, plants treated e.g. with compound no. 1.1, 1.2, 1.3, 1.4, 1.5, 1.34, 1.39, 1.46, 1.79, 1.81, 1.86, 1.101, 1.116, 1.136, 1.139, 1.140, 1.144, 2.5, 3.29, 7.6 or 7.26 remain virtually completely free of Colletotrichum (20 to 0% attack).

Example 3.2: Comparison test: direct action against *Colletotrichum lagenarium*

The formulated test compound is mixed at various concentrations (100, 10, 1, 0.1 ppm) with nutrient substrate (vegetable juice) which has been autoclaved and cooled and which contains $10^3$ spores/ml, and the mixture is poured onto microtiter plates. The plates are then incubated in the dark at 22° C. After 2–3 days the growth of the fungus is measured by spectrophotometry and the $EC_{50}$ values are determined.

In the case of e.g. compound 1.1, 1.2, 1.4, 1.34, 1.39, 1.79, 1.81, 1.86, 1.100, 1.101, 1.116, 1.135, 1.136, 1.139, 1.140, 1.144, 2.5, 3.26, 3.29 or 7.6, no inhibition of the growth of the fungus is observed. In contrast, when the fungicide benomyl (commercially available product)

is used as comparison substance at 0.2 ppm, a 50 % inhibition ($EC_{50}$) of *Colletotrichum lagenarium* occurs.

Example 3.3: Immunising action against *Pyricularia oryzae* on rice plants

A) Foliar application

After a cultivation period of 3 weeks, rice plants are treated by foliar application with a spray mixture (concentration: 0.02% active ingredient) prepared from a wettable powder formulation of the test compound. After 2–3 days the plants are inoculated with a spore suspension (350,000 spores/ml) and incubated for 7 days at high humidity and at a temperature of 24° C. Evaluation of the protective action is made 7–8 days after inoculation and is based on the fungus attack.

Untreated and infected control plants exhibit 100% attack in this test.

Compounds of Tables 1 to 8 result in good immunisation against *Pyricularia oryzae*. Thus, plants treated e.g. with compound 1.2, 1.34, 1.37, 1.38, 1.39, 1.72, 1.79, 1.86, 1.96, 1.103, 1.119, 1.135, 2.2, 2.3, 3.1, 3.2, 3.8, 3.9, 3.13, 4.2, 5.2 or 7.2 remain virtually completely free of *Pyricularia oryzae* (20 to 0 % attack).

B) Soil application

After a cultivation period of 3 weeks, rice plants are treated by soil application with a spray mixture (concentration: 0.002% active ingredient, based on the volume of the soil) prepared from a wettable powder formulation of the test compound. After 2–3 days the plants are inoculated with a spore suspension ($35\times10^5$ spores/ml) and incubated for 7 days at high humidity and at a temperature of 24° C.

Evaluation of the protective action is made 7 to 8 days after inoculation and is based on the fungus attack.

Untreated and infected control plants exhibit 100% attack in this test. Compounds of Tables 1 to 7 exhibit good activity against *Pyricularia oryzae*. Thus, plants treated e.g. with compounds 1.2, 1.34, 1.37, 1.38, 1.39, 1.79, 1.96, 1.103, 1.119, 1.135, 2.2, 2.3, 3.1, 3.9, 3.13 or 7.3 remain virtually completely free of *Pyricularia oryzae* (20 to 0% attack).

Example 3.4: Comparison test: direct action against *Pyricularia oryzae*

The formulated test compound is mixed at various concentrations (100, 10, 1, 0.1 ppm) with nutrient substrate (vegetable juice) which has been autoclaved and cooled and which contains 103 spores/ml, and the mixture is poured onto microtiter plates. The plates are incubated in the dark at 22° C. After 2–3 days the growth of the fungus is determined by spectrophotometry.

In the case of e.g. compound 1.1, 1.2, 1.3, 1.4, 1.5, 1.34, 1.37, 1.39, 1.72, 1.86, 1.96, 1.100, 1.101, 1.103, 1.108, 1.140, 2.5, 3.1, 3.9, 3.26, 7.26 or 7.6, no inhibition of the growth of the fungus is observed. In contrast, when the fungicide benomyl (commercially available product/see Example 3.2) is used as comparison substance at 0.1 ppm, a 50% inhibition ($EC_{50}$) of *Pyricularia oryzae* occurs.

Example 3.5: Immunising action against *Pseudomonas lachrymans* on *Cucumis sativus* L.

A) Foliar application

After a cultivation period of 2 weeks, cucumber plants are sprayed with a spray mixture (concentration: 0.02% active ingredient) prepared from a wettable powder formulation of the test compound.

After one week the plants are infected with a bacteria suspension ($10^8$ bacteria/ml) and incubated for 7 days at high humidity and at a temperature of 23° C.

Evaluation of the protective action is made 7 to 8 days after infection and is based on the bacteria attack.

Compounds of Tables 1 to 7 result in good immunisation against *Pseudomonas lachrymans*. Thus, plants treated e.g. with compound 1.2, 1.3, 1.4, 1.5, 1.9, 1.34, 1.38, 1.46, 1.72, 1.79, 1.81, 1.119, 1.135, 2.2, 2.3, 3.1, 3.28, 3.29 or 7.26 remain substantially free of Pseudomonas (20 to 0% attack).

B) Soil application

After a cultivation period of 2 weeks, cucumber plants are treated by soil application with a spray mixture (concentration: 0.002% active ingredient, based on the volume of the soil) prepared from a wettable powder formulation of the test compound.

After one week the plants are infected with a bacteria suspension ($10^8$ bacteria/ml) and incubated for 7 days at high humidity and at a temperature of 23° C.

Evaluation of the protective action is made 7 to 8 days after infection and is based on the bacteria attack.

Compounds of Tables 1 to 7 result in good immunisation against *Pseudomonas lachrymans*. Thus, plants treated e.g. with compound 1.1, 1.2, 1.3, 1.4, 1.5, 1.9, 1.34, 1.38, 1.46, 1.72, 1.79, 1.81, 1.119, 1.135, 2.2, 2.3, 3.1, 3.9, 3.28, 3.29 or 7.26 remain virtually completely free of Pseudomonas (20 to 0% attack).

Untreated and infected control plants exhibit 100% attack of the disease in tests A and B.

Example 3.6: Comparison test: direct action against *Pseudomonas lachrymans*

The formulated test compound is mixed at various concentrations (100, 10, 1, 0.1 ppm) with nutrient broth (0.8%) which has been autoclaved and cooled and which contains $10^6$ bacteria/ml, and the mixture is poured onto microtiter plates. The plates are then incubated in the dark at 22° C. on a vibrator table (120 rpm). After an incubation period of 2–3 days the growth of the bacteria is determined by spectrophotometry.

In the case of e.g. compound 1.1, 1.2, 1.3, 1.4, 1.5, 1.34, 1.38, 1.72, 1.79, 1.81, 1.96, 1.101, 1.119, 1.140, 2.2, 2.3, 2.5, 3.1, 3.6, 3.9, 3.26, 3.28, 3.29 or 7.26, no inhibition of the growth of the bacteria is observed. In contrast, when the bactericide streptomycin is used as comparison substance at 0.4 ppm, a 50% inhibition ($EC_{50}$) of *Pseudomonas lachrymans* occurs.

Example 3.7: Immunising action against *Xanthomonas oryzae* on rice plants

A) Foliar application

After a cultivation period of 3 weeks, rice plants are treated by foliar application with a spray mixture (concentration: 0.02% active ingredient) prepared from a wettable powder formulation of the test compound. After 2–3 days the plants are inoculated with a bacteria suspension ($10^8$ bacteria/ml) and incubated for 7 days at high humidity and at a temperature of 24° C. Evaluation of the protective action is made 7–8 days after inoculation and is based on the bacteria attack.

Compounds of the Tables result in good immunisation against *Xanthomonas oryzae*. Thus, plants treated e.g. with compound 1.3, 1.5, 1.16, 1.37, 1.38, 1.72, 1.81, 1.86, 1.95, 1.102, 1.103, 1.108, 1.136, 1.139, 2.2, 2.5 or 3.29 remain virtually completely free of *Xanthomonas oryzae* (20 to 0% attack).

B) Soil application

After a cultivation period of 3 weeks, rice plants are treated by soil application with a spray mixture (concentration: 0.002% active ingredient, based on the volume of the soil) prepared from a wettable powder formulation of the test compound. After 2–3 days the plants are inoculated with a bacteria suspension ($10^8$ bacteria/ml) and incubated for 7 days at high humidity and at a temperature of 24° C.

Evaluation of the protective action is made 7–8 days after inoculation and is based on the bacteria attack.

Compounds of Tables 1 to 7 result in good immunisation against *Xanthomonas oryzae*. Thus, plants treated e.g. with compound 1.2, 1.3, 1.4, 1.5, 1.6, 1.9, 1.16, 1.34, 1.35, 1.38, 1.44, 1.46, 1.68, 1.71, 1.72, 1.81, 1.86, 1.96, 1.102, 1.103, 1.119, 1.135, 1.136, 2.2, 2.3, 2.5, 3.1, 3.13, 3.28, 3.29, 7.2, 7.5 or 7.26 remain virtually completely free of *Xanthomonas oryzae* (20 to 0% attack).

Untreated and infected control plants exhibit 100% attack in tests A and B.

Example 3.8: Comparison test: direct action against *Xanthomonas oryzae*

The formulated test compound is mixed at various concentrations (100, 10, 1, 0.1 ppm) with nutrient broth (0.8%) which has been autoclaved and cooled and which contains $10^6$ bacteria/ml, and the mixture is poured onto microtiter plates. The plates are incubated in the dark at 22° C. on a vibrator table (120 rpm). After 2–3 days the growth of the bacteria is determined by spectrophotometry.

In the case of e.g. compound 1.1, 1.2, 1.3, 1.4, 1.5, 1.9, 1.34, 1.38, 1.81, 1.101, 1.119, 1.135, 1.140, 2.3 or 2.5, no inhibition of the growth of the bacteria is observed. In contrast, when the bactericide streptomycin is used as comparison substance at 0.4 ppm, a 50% inhibition ($EC_{50}$) of *Xanthomonas oryzae* occurs.

Example 3.9: Immunising action against *Xanthomonas vesicatoria* on paprika plants A) Foliar application After a cultivation period of 4 weeks, paprika plants are treated by foliar application with a spray mixture (concentration: 0.02% active ingredient) prepared from a wettable powder formulation of the test compound. After 2–3 days the plants are inoculated with a bacteria suspension ($10^8$ bacteria/ml) and incubated for 6 days at high humidity and at a temperature of 25° C. Evaluation of the protective action is made 7–8 days after inoculation and is based on the bacteria attack.

Untreated and infected control plants exhibit 100% attack in this test.

Compounds of Tables 1 to 7 result in good immunisation against *Xanthomonas vesicatoria*. Thus, plants treated e.g. with compound 1.2, 1.5, 1.9, 1.16, 1.34, 1.35, 1.37, 1.72, 1.81, 1.86, 1.96, 1.102, 1.103, 1.108, 1.136, 3.1, 3.13, 3.28, 3.29, 5.2, 7.26 or 7.5 remain virtually completely free of *Xanthomonas vesicatoria* (20 to 0% attack).

B) Soil application

After a cultivation period of 4 weeks, paprika plants are treated by soil application with a spray mixture (concentration: 60 ppm, based on the volume of the soil) prepared from a wettable powder formulation of the test compound. After 2–3 days the plants are inoculated with a bacteria suspension ($10^8$ bacteria/ml) and incubated for 6 days at high humidity and at a temperature of 25° C.

Evaluation of the protective action is made 7–8 days after inoculation and is based on the bacteria attack.

Untreated and infected control plants exhibit 100 % attack in this test.

Compounds of Tables 1 to 7 result in good immunisation against *Xanthomonas vesicatoria*. Thus, plants treated e.g. with compound 1.2, 1.5, 1.6, 1.9, 1.11, 1.16, 1.34, 1.35, 1.36, 1.37, 1.39, 1.68, 1.71, 1.72, 1.81, 1.86, 1.95, 1.100, 1.102, 1.103, 1.108, 1.116, 1.140, 1.144, 2.5, 3.1, 3.13, 3.28, 3.29, 5.2, 7.2 or 7.26 remain virtually completely free of *Xanthomonas vesicatoria* (20 to 0% attack).

Example 3.10: Immunising action against *Phytophthora infestans* on tomato plants A) Foliar application After a cultivation period of 3 weeks, tomato plants are sprayed with a spray mixture (0.02% active ingredient) prepared from a wettable powder formulation of the test compound. After 2–3 days the treated plants are infected with a *sporangia* suspension of the fungus ($5\times10^4$ *sporangia*/ml). Evaluation of the protective action is made after incubation of the infected plants for 5 days at 90–100% relative humidity and 20° C.

Untreated and infected control plants exhibit 100 % attack in this test.

Compounds of Tables 1 to 7 result in good immunisation against *Phytophthora infestans*. Thus, plants treated e.g. with compound 1.6, 1.16, 1.34, 1.44, 1.68, 1.71, 1.72, 1.96, 1.101, 3.9 or 7.26 remain substantially free of Phytophthora (20 to 0% attack).

B) Soil application

After a cultivation period of 3 weeks, a spray mixture (0.006% active ingredient, based on the volume of the soil) prepared from a wettable powder formulation of the test compound is poured onto tomato plants. Care is taken that the spray mixture does not come into contact with the parts of the plants above the soil. After 4 days the treated plants are infected with a *sporangia* suspension ($5\times10^4$ *sporangia*/ml) of the fungus. Evaluation of the protective action is made after incubation of the infected plants for 5 days at 90–100% relative humidity and 20° C.

Untreated and infected control plants exhibit 100 % attack in this test.

Compounds of Tables 1 to 7 result in good immunisation against *Phytophthora infestans*. Thus, plants treated e.g. with compound 1.6, 1.34, 1.44, 1.68, 1.71, 1.72, 1.101, 3.2, 3.4, 3.6, 3.8, 3.9, 3.13 or 7.26 remain substantially free of Phytophthora (20 to 0% attack).

Example 3.11: Comparison test: direct action against *Phytophthora infestans*

The formulated test compound is mixed at various concentrations (100, 10, 1, 0.1 ppm) with nutrient substrate (peas/agar) which has been sterile-filtered and contains $10^6$ *sporangia*/ml, and the mixture is poured onto microtiter plates. The plates are incubated in the dark at 22° C. After 2–3 days the growth of the fungus is determined by spectrophotometry.

In the case of e.g. compound 1.1, 1.2, 1.4, 1.34, 1.72, 1.86, 1.104, 1.108, 1.116, 1.135, 1.140, 1.144, 2.5, 3.1, 3.6, 3.9, 3.13, 3.26, 7.6 or 7.26, no inhibition of the growth of the fungus is observed. In contrast, when ridomil (commercially available product) is used as comparison substance at 0.2 ppm, a 50% inhibition of Phytophthora infestans occurs.

Example 3.12: Immunising action against *Plasmopara viticola* on vines

Vine seedlings in the 4- to 5-leaf stage are sprayed with a spray mixture (0.02% active ingredient) prepared from a wettable powder formulation of the test compound. After one week the treated plants are infected with a *sporangia* suspension ($5\times10^4$ sporangia/ml) of the fungus. Evaluation of the protective action is made after incubation for 6 days at 95–100% relative humidity and 20° C.

Untreated and infected control plants exhibit 100 % attack in this test.

Compounds of Tables 1 to 8 result in good immunisation against *Plasmopara viticola*. Thus, vines treated e.g. with compound 1.1, 1.2 or 1.5 remain substantially free of *Plasmopara viticola* (20 to 0% attack).

Example 3.13: Immunising action against Pseudomonas tomato on tomato plants

A) Foliar application

After a cultivation period of 3 weeks, tomato plants are treated by foliar application with a spray mixture (concentration: 0.02% active ingredient) prepared from a wettable powder formulation of the test compound. After 2–3 days the plants are inoculated with a bacteria suspension ($10^8$ bacteria/ml) and incubated for 6 days at high humidity and at a temperature of 25° C. Evaluation of the protective action is made 7–8 days after inoculation and is based on the bacteria attack.

Untreated and infected control plants exhibit 100 % attack in this test.

Compounds of Tables 1 to 8 result in good immunisation against *Pseudomonas tomato*. Thus, plants treated e.g. with compound 1.16, 1.95 or 7.5 remain substantially free of Pseudomonas (20 to 0% attack).

B) Soil application

After a cultivation period of 3 weeks, tomato plants are treated by soil application with a spray mixture (concentration: 0.002% active ingredient, based on the volume of the soil) prepared from a wettable powder formulation of the test compound. After 2–3 days the plants are inoculated with a bacteria suspension ($10^8$ bacteria/ml) and incubated for 6 days at high humidity and at a temperature of 25° C.

Evaluation of the protective action is made 7–8 days after inoculation and is based on the bacteria attack.

Untreated and infected control plants exhibit 100 % attack in this test.

Compounds of Tables 1 to 7 result in good immunisation against Pseudomonas tomato. Thus, plants treated e.g. with compound 1.44, 1.95 or 7.5 remain virtually completely free of Pseudomonas (20 to 0% attack).

Example 3.14: Immunising action against *Phytophthora parasitica* var. *nicotianae* on tobacco plants Soil application Tobacco plants (8 weeks old) are treated with a formulated solution of the test compound by soil application (concentration: 2 ppm, based on the volume of the soil) or by injection into the leaf (concentration: 0.02% active ingredient). After 4 days the plants are infected with *Phytophthora parasitica*. 2 ml of a zoospore suspension ($8\times10^4$ z/ml) are pipetted around the base of the stalk and washed into the soil with water. The plants are kept at 24°–26° C. for 3 weeks.

Evaluation of the symptoms is made on the basis of the degree to which the plants have withered.

Untreated and infected plants had withered completely.

Compounds of Tables 1 to 7 exhibit good activity against *Phytophthora parasitica*. Thus e.g. compound 1.2 reduces withering to 0–5%.

Example 3.15: Direct action against *Phytophthora parasitica* var. *nicotianae*

The test compound is mixed with nutrient substrate (V-8 agar) at a concentration of 100 ppm and the mixture is poured into Petri dishes. After cooling, either a disc of mycelia (8 mm) is placed in the centre of the plate or 100 pl of a zoospore suspension ($10^5$ spores/ml) of the fungus are spread onto the plate. The plates are incubated at 22° C.

Compound 1.2 exhibits no inhibiting activity on the germination and growth of the fungus in comparison with the control plates without active ingredient.

Example 3.16: Immunising action against *Peronospora tabacina* on tobacco plants A) Foliar application Tobacco plants (8 weeks old) are sprayed with a formulated solution of the test compound (concentration: 0.02% active ingredient). 4 days after the treatment the plants are inoculated with a sporangia suspension of *Peronospora tabacina* ($10^4$ sporangia/ml), kept in the dark for 20 hours at 25° C. and high humidity, and then incubated further with normal day/night alternation.

B) Soil application

Tobacco plants (8 weeks old) are treated by soil application with a formulated solution of the test compound (concentration: 0.006% active ingredient, based on the volume of the soil). After 4 days the plants are inoculated with a sporangia suspension of *Peronospora tabacina* ($10^4$ sporangia/ml), kept in the dark for 20 hours at 25° C. and high humidity, and then incubated further with normal day/night alternation.

In tests A and B evaluation of the symptoms is made on the basis of the area of the leaf surface attacked by the fungus.

The control plants exhibit 90 to 100% attack. Plants treated in tests A and B with compound 1.2 exhibit 0–35% attack.

Example 3.17: Direct action against *Peronospora tabacina*

Formulated test compound is mixed at various concentrations (10, 1, 0.1 ppm) with water agar and the mixture is poured into Petri dishes. After cooling, 100 pl of a sporangia suspension ($10^6$ spores/ml) are spread onto the plate. The plates are incubated at 18° C. for 16 hours.

In the case of e.g. compound 1.2, no inhibition of the germination of *Peronospora tabacina* is observed.

Example 3.18: Immunising action against *Cercospora nicotianae* on tobacco plants A) Foliar application Tobacco plants (8 weeks old) are sprayed with a formulated solution of the test compound (concentration: 200 ppm). Four days after the treatment the plants are inoculated with a spore suspension of *Cercospora nicotianae* ($10^5$ spores/ml) and incubated for 5 days at high humidity and at a temperature of 22°–25° C. Incubation is then continued at normal humidity and at 20°–22° C.

B) Soil application

Tobacco plants (8 weeks old) are treated by soil application with a formulated solution of the test compound (concentration: 0.002% active ingredient). After 4 days the plants are inoculated with a spore suspension of *Cercospora nicotianae* ($10^5$ spores/ml) and incubated for 5 days at high humidity and at a temperature of 22°–25° C. Incubation is then continued at normal humidity and at 20°–22° C.

In tests A and B evaluation of the symptoms is made on the basis of the fungus attack 12 to 14 days after infection.

The control plants exhibit 100% attack. Plants treated in tests A and B with compound 1.2 exhibit 0–20% attack.

Example 3.19: Direct action against *Cercospora nicotianae*

Test compound is mixed at various concentrations (100, 10, 1, 0.1 ppm) with nutrient substrate (V-8 agar) and the mixture is poured into Petri dishes. After cooling, either a disc of mycelia (8 mm) is placed in the centre of the plate or 100 pl of a spore suspension ($5\times10^4$ spores/ml) are spread onto the plate. The plates are incubated at 22° C.

Compound 1.2 exhibits no inhibiting activity on the germination and growth of the fungus in comparison with the control plates without active ingredient.

Example 3.20: Immunising action against *Pseudomonas tabaci* on tobacco plants

A) Foliar application

Tobacco plants (8 weeks old) are treated with a formulated solution of the test compound by spraying (concentration: 200 ppm) or by injection (concentration: 200, 60, 20 ppm). After 4 days the plants are sprayed with a bacteria suspension ($2\times10^7$ bacteria/ml) and kept at high humidity and 22°–25° C. for 3 days. Incubation is then continued for 3 days at normal humidity and 22°–25° C.

B) Soil application

Tobacco plants {8 weeks old) are treated by soil application with a formulated solution of the test compound (concentration: 0.002% to 0.0002% active ingredient). After 4 days the plants are sprayed with a bacteria suspension ($2\times10^7$ bacteria/ml) and kept at high humidity and 22°–25° C. for 3 days. Incubation is then continued for 3 days at normal humidity and 22°–25° C.

In tests A and B evaluation of the symptoms is made on the basis of the bacteria attack.

The control plants exhibit 100% attack.

Plants treated in tests A and B with compound 1.2 or 1.46 exhibit 0–20% attack.

Example 3.21: Direct action against *Pseudomonas tabaci*

The test compound is mixed at various concentrations (100, 10, 1, 0.1 ppm) with liquid nutrient substrate (nutrient broth) containing $10^6$ bacteria/ml, and the mixture is poured onto microtiter plates. The plates are incubated at 22° C. and the growth of the bacteria is determined after 16 hours by measuring the optical density.

In the case of e.g. compound 1.2, no inhibition of the growth of *Pseudomonas tabaci* is observed. In contrast, streptomycin causes a 50% inhibition ($EC_{50}$) of growth at 0.1 ppm.

Example 3.22: Immunising action against tobacco mosaic virus and potato Y-virus on tobacco plants Tobacco plants (8 weeks old) are treated with a formulated solution of the test compound by spraying (concentration: 200 ppm) or by injection (concentration: 0.02 % to 0.0002% active ingredient). After 4 days the plants are inoculated by mechanical means with a suspension of tobacco mosaic virus (0.5 μg/ml + Carborundum) or of potato Y-virus (juice of an infected leaf, 1 g/100 ml $H_2O$+ Carborundum) and incubated at a temperature of 20°–22° C.

Evaluation of the protective action is made in the case of tobacco mosaic virus on the basis of the number and size of local lesions 7 days after inoculation and in the case of potato Y-virus by serological determination of the number of viruses 7 and 10 days after inoculation.

In the test, plants treated with compound 1.2 exhibit, in the case of tobacco mosaic virus, 88 to 100% inhibition of the development of lesions in comparison with the corresponding controls (100% damage) and, in the case of potato Y-virus, 70 to 100% inhibition of the increase of the virus in comparison with the corresponding controls (=100%). The untreated and infected plants exhibit 100% lesions (control).

Example 3.23: Direct action against tobacco mosaic virus

The formulated test compound is added directly to the tobacco mosaic virus inoculum (200 ppm+0.5 μg/ml virus+ Carborundum). After one hour, tobacco plants (8 weeks old) are inoculated with the mixture by mechanical means.

Plants inoculated with this mixture of tobacco mosaic virus and compound 1.2 exhibit no protective action.

Example 3.24: Immunising action against *Erysiphe graminis* on wheat

After a cultivation period of 5 days, wheat plants are sprayed with a spray mixture (concentration: 0.02%) prepared from a wettable powder formulation of the test compound. One day later the plants are infected with conidia of *Erysiphe graminis* and incubated at 20° C.

Evaluation of the protective action is made 8–10 days after infection and is based on the fungus attack.

Compounds of Tables 1 to 8 used as active ingredient exhibit good activity against *Erysiphe graminis* in this test. Thus, plants treated e.g. with compound 1.2 remain substantially free of Erysiphe attack (0 to 20% damage). On the other hand, Erysiphe attack is 100% in untreated and infected plants (control).

Example 3.25a: In vitro test of direct action against *Pyricularia oryzae*, *Colletotrichum lagenarium* or *Phytophthora infestans*

The active ingredient of the test compounds is added a) to a liquid V-8 medium (vegetable mixture) containing $10^4$ spores/ml of *Pyricularia oryzae* or *Colletotrichum lagenarium* and b) to a liquid pea medium containing $10^4$ sporangia/ml of *Phytophthora infestans*, the final concentration of active ingredient in both cases being 60 ppm. The prepared nutrient media are placed on microtiter plates and kept there in the dark for 2 days at 22° C. and 100% relative humidity, the preparations containing *Pyricularia oryzae* and Colletotrichum being shaken.

The growth of the fungi is then determined by spectrometric absorption measurement of the media at 595 nm (turbidity measurement).

Example 3.25b: In vitro test of direct action against *Xanthomonas oryzae* and *Pseudomonas lachrymans*

The active ingredient of the test compounds is added to a nutrient medium (Bacto-Nutrient Broth Difco) containing $10^6$ organisms/ml of *Xanthomonas oryzae* or *Pseudomonas lachrymans*, the final concentration of active ingredient being 60 ppm. The prepared nutrient medium is placed on microtiter plates and shaken there in the dark for 2 days at 22° C. and 100% relative humidity.

The growth of the bacteria is then determined by spectrometric absorption measurements of the media at 595 nm (turbidity measurement).

During testing of the active ingredient in the above-described tests, control experiments are carried out in parallel in the manner described, but without using active ingredients. The degree of turbidity measured in the control experiments represents the 100% value for the evaluation scale used.

Evaluation is made on the basis of the following scale of ratings: Growth of fungus (in %) Rating

| Growth of fungus (in %) | Rating |
|---|---|
| 81–100 | 9* |
| 71–80 | 8* |
| 61–70 | 7* |
| 51–60 | 6 |
| 41–50 | 5 |
| 31–40 | 4 |
| 21–30 | 3 |
| 11–20 | 2 |
| 0–10 | 1 |

*In the case of ratings greater than or equal to 7, it is concluded that there is no direct microbicidal activity.

Fungicidal or bactericidal in vitro action of compounds of formula I in comparison with known substances a) Test compounds of formula

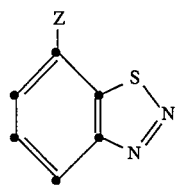

| Comp. no. | Z | Colletotrichum lagenarium | Pyricularia oryzae | Phytophthora infestans | Xanthomonas oryzae | Pseudomonas lachrymans |
|---|---|---|---|---|---|---|
| 1.1 | COOH | 9 | 9 | 9 | 9 | 9 |

-continued

Fungicidal or bactericidal in vitro action of compounds of formula I in comparison with known substances a) Test compounds of formula

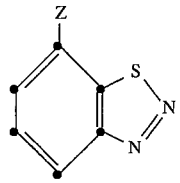

| Comp. no. | Z | Colletotrichum lagenarium | Pyricularia oryzae | Phytophthora infestans | Xanthomonas oryzae | Pseudomonas lachrymans |
|---|---|---|---|---|---|---|
| 1.2 | COOMethyl | 9 | 9 | 9 | 9 | 9 |
| 1.4 | COO-n-propyl | 9 | 9 | 9 | 9 | 9 |
| 1.135 | COO-cyclohexyl | 6 | — | 9 | 9 | — |
| 1.34 | COO-Benzyl | 9 | 9 | 9 | 9 | 9 |
| 1.96 | COO—CH$_2$-2'Furyl | — | 9 | 4 | — | 9 |
| 2.5 | COS-Benzyl | 9 | 9 | 9 | 9 | 9 |
| 1.101 | COOCH$_2$-2-Pyridinyl | 9 | 9 | 6 | 9 | 9 |
| 1.140 | COOCH$_2$-2-Methylphenyl | 9 | 9 | 9 | 9 | 9 |
| 1.144 | COOCH$_2$-3-Methoxyphenyl | 9 | — | 9 | 9 | — |
| 1.116 | COOCH$_2$-1-Naphthyl | 9 | — | 9 | 6 | — |
| 1.108 | COOCH$_2$CH$_2$P(O)(OMethyl)$_2$ | — | 9 | 9 | — | 9 |
| 1.104 | COOCH$_2$CH$_2$Si(Methyl)$_3$ | — | 3 | 9 | — | 9 |
| 1.72 | COO—N=⟨pyridyl⟩ | — | 9 | 9 | — | 9 |
| 1.86 | COO-Diaceton-D-glucosidyl | — | 9 | 9 | — | 9 |
| 3.1 | CONH$_2$ | — | 9 | 9 | — | 9 |
| 3.26 | CON(allyl)$_2$ | — | 9 | 9 | — | 8 |
| 3.13 | CON[CH$_2$CH$_2$CN]$_2$ | — | 6 | 9 | — | 9 |
| 1.100 | COOCH$_2$—N⟨triazole⟩ | 9 | 9 | — | 9 | — |
| 3.6 | CONH-Phenyl | — | — | 9 | — | 9 |
| 3.9 | CONH—CH$_2$COOH | — | 9 | 9 | — | 9 |
| 7.26* | CN | — | 9 | 9 | — | 8 | b) Test compounds of formulae

| Verb. Nr. | Formel | Colletotrichum lagenarium | Pyricularia oryzae | Phytophthora infestans | Xanthomonas oryzae | Pseudomonas lachrymans |
|---|---|---|---|---|---|---|
| 7.6 | F-benzothiadiazole-COOCH$_3$ | — | 9 | 9 | — | 8 |
| * | Cl-benzothiadiazole-NO$_2$ | 1 | 1 | 1 | — | — |

| | b) Test compounds of formulae | | | | |
|---|---|---|---|---|---|
| Verb. Nr. | Formel | Colletotrichum lagenarium | Pyricularia oryzae | Phytophthora infestans | Xanthomonas oryzae | Pseudomonas lachrymans |
| * | 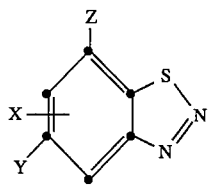 | 1 | 1 | 1 | — | — |

*Compounds from DE-OS 1 695 786

What is claimed is:

1. A compound of the formula

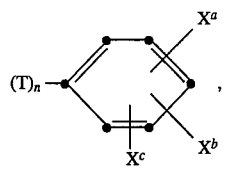

in which

X is hydrogen, Y is hydrogen, Z is COA; A is UR, R is hydrogen, $C_1$–$C_8$alkyl, $C_1$–$C_8$alkyl substituted by halogen, cyano, nitro, hydroxy or by U-$C_1$–$C_3$alkyl, (T)-COOH or (T)-COO$C_1$–$C_4$alkyl, $C_3$–$C_6$-alkenyl, halosubstituted $C_3$–$C_6$alkenyl, $C_3$–$C_6$alkynyl, halosubstituted $C_3$–$C_6$alkynyl, $(T)_n$-$C_3$–$C_8$cycloalkyl, or a group selected from the following:

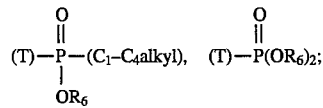

$(T)_n$-napht, $(T)_n$-Si($c_1$–$C_8$alkyl)$_3$, $$(T)-\overset{O}{\underset{OR_6}{\overset{\|}{P}}}-(C_1-C_4\text{alkyl}), \quad (T)-\overset{O}{\overset{\|}{P}}(OR_6)_2;$$

and $(T)_nW$;

each of $X^a$, $X^b$ and $X^c$ independently of the others, is hydrogen, halogen, hydroxy, cyano, HOOC, MOOC, $C_1$–$C_3$alkyl-OOC, $C_1$–$C_4$alkyl, $C_1$–$C_4$alkoxy, $C_1$–$C_2$haloalkyl having up to 5 halogen atoms or $X^a$ is $C_1$–$C_2$haloalkoxy having up to 5 halogen atoms, nitro, dimethylamino phenyl, phenoxy, benzyloxy or sulfamoyloxy and $X^b$ and $X^c$ are both hydrogen; or $X^a$ is phenyl, phenoxy or benzyloxy and $X^b$ is halogen or methyl and $X^c$ is hydrogen; or $X^a$, $X^b$ and $X^c$ together are 4 or 5 fluorine atoms; napht is a naphthyl radical that is unsubstituted or is substituted by halogen, methyl, methoxy or by nitro; W is a 5- to 7-membered saturated or unsaturated heterocycle having from 1 to 3 hetero atoms from the group O, N and S that is unsubstituted or is substituted by halogen, trifluoromethyl, cyano, $C_1$–$C_2$alkyl or by a $C_1$–$C_2$-alkoxycarbony-$C_2$–$C_4$alkyleneimino radical, or is a monosaccharide radical; T is a bridge member —$CH_2$—, —$CH_2CH_2$—, —$CH(CH_3)$—, —$CH_2CH_2CH_2$— or —$CH_2CH_2O$—; $R_6$ is hydrogen or $C_1$–$C_4$alkyl; and n is 0 or 1; or salt thereof with amines or inorganic bases.

2. A compound according to claim 1 selected from the group:

7-(methylthiocarbonyl)-benzo-1,2,3-thiadiazole (Compound 2.1 ); 7-(ethylthiocarbonyl)-benzo-1,2,3-thiadiazole (Compound 2.2); 7-(n-propylthiocarbonyl)-benzo-1,2,3-thiadiazole (Compound 2.3) and 7-(benzylthiocarbonyl)-benzo-1,2,3-thiadiazole (Compound 2.5).

3. A composition for protecting plants against attack by phytopathogenic microorganisms, containing as active ingredient 1,2,3-benzothiadiazole-7-carboxylic acid or a salt thereof with an inorganic or organic cation together with a suitable carrier.

4. The compound of claim 1 7-(methylthiocarbonyl)-benzo-1,2,3-thiadiazole.

* * * * *